US009976129B2

(12) United States Patent
Kamiya et al.

(10) Patent No.: US 9,976,129 B2

(45) Date of Patent: May 22, 2018

(54) FUSION PROTEIN FOR PROTEIN DETECTION, AND METHOD FOR DETECTING PROTEIN

(71) Applicants: Kyushu University, National University Corporation, Fukuoka-shi, Fukuoka (JP); Hitachi, Ltd., Tokyo (JP)

(72) Inventors: Noriho Kamiya, Fukuoka (JP); Kyoichi Matsuba, Mitaka (JP); Kenji Nagai, Mitaka (JP); Kounosuke Hayashi, Mitaka (JP)

(73) Assignees: KYUSHU UNIVERSITY, NATIONAL UNIVERSITY CORPORATION, Fukuoka (JP); Hitachi, Ltd., Tokyo (JP)

( * ) Notice: Subject to any disclaimer, the term of this patent is extended or adjusted under 35 U.S.C. 154(b) by 1 day.

(21) Appl. No.: 15/029,787

(22) PCT Filed: Oct. 6, 2014

(86) PCT No.: PCT/JP2014/077274

§ 371 (c)(1),
(2) Date: Apr. 15, 2016

(87) PCT Pub. No.: WO2015/056659

PCT Pub. Date: Apr. 23, 2015

(65) Prior Publication Data

US 2016/0355791 A1 Dec. 8, 2016

(30) Foreign Application Priority Data

Oct. 18, 2013 (JP) ................................ 2013-217048

(51) Int. Cl.
*C12N 9/16* (2006.01)
*G01N 33/68* (2006.01)

(52) U.S. Cl.
CPC ........ *C12N 9/16* (2013.01); *C12Y 301/03001* (2013.01); *G01N 33/6803* (2013.01); *C07K 2319/00* (2013.01); *C07K 2319/21* (2013.01); *C07K 2319/61* (2013.01)

(58) Field of Classification Search
CPC ............ C07K 2319/00; C07K 2317/21; C12Y 301/03001
See application file for complete search history.

(56) References Cited

U.S. PATENT DOCUMENTS

| | | | |
|---|---|---|---|
| 5,891,699 | A | 4/1999 | Boulain et al. |
| 2010/0291586 | A1 | 11/2010 | Bedouelle |

FOREIGN PATENT DOCUMENTS

| | | | |
|---|---|---|---|
| EP | 0441252 | A2 | 8/1991 |
| EP | 0752475 | A1 | 1/1997 |
| EP | 2003144 | A1 | 12/2008 |
| JP | 9-98780 | A | 4/1997 |
| JP | 2620416 | B2 | 6/1997 |
| JP | 3560972 | B2 | 9/2004 |
| JP | 2014-100095 | A | 6/2014 |
| WO | 94/01531 | A1 | 1/1994 |

OTHER PUBLICATIONS

Bradshaw et al. 1981; Amino acid sequence of *Escherichia coli* alkaline phosphatase. PNAS 78(6): 3473-3477.*

Guss et al. 1986; Structure of the IgG-binding regions of streptococcal protein G. EMBO Journal. 5(7): 1567-1575.*

Jansson et al. 1998; All individual domains of staphylococcal protein A show Fab binding. FEMS Immunology and Medical Microbiology 20: 69-78.*

International Search Report from International Application No. PCT/JP14/77274 dated Jan. 20, 2015.

Y. Maeda, "Engineering of Functional Chimeric Protein G-Vargula Luciferase", Analytical Biochemistry, 249(2), pp. 147-152 (1997).

C. Goward, et al., "Expression and Purification of a Truncated Recombinant Streptococcal Protein G", Biochem. J., (1990)267, 171-177.

B. Muller, et al., "Improving *Escherichia coli* Alkaline Phosphatase Efficacy by Additional Mutations inside and outside the Catalytic Pocket", Chembiochem 2001, 2, 517-523.

S. Sun, et al., "Chimaeric Protein A/protein G and protein G/alkaline phosphatase as reporter molecules", Journal of Immunol. Methods, Jul. 31, 1992, vol. 152, No. 1, p. 43-48.

O.B. Gorbatiuk, et al., "Construction, expression, functional characterization and practical application of fusion protein SPA-BAPmut", Biopolym. Cell, Feb. 2013, vol. 29, p. 49-54.

M. Eliasson, et al., "Chimeric IgG-binding Receptors Engineered from Staphylococcal Protein A and Streptococcal Protein G", The Journal of Biological Chemistry, vol. 263, No. 9, Issue of Mar. 25, 1988, pp. 4323-4327.

Notice of Grounds of Rejection dated Jan. 13, 2015 from JP2013-217048.

Written Opinion of the International Searching Authority dated Jan. 20, 2015.

International Search Report from International Application No. PCT/JP14/77274 dated Mar. 6, 2017.

(Continued)

*Primary Examiner* — Karen Cochrane Carlson

(74) *Attorney, Agent, or Firm* — Brundidge & Stanger, P.C.

(57) ABSTRACT

A fusion protein for protein detection in which are fused: a protein domain including at least one among a C1 domain of protein G, a C2 domain of protein G, and a C3 domain of protein G; and a double mutant D153G/D330N of *Escherichia coli* alkaline phosphatase (BAP) in which the 153 amino acid residue Asp has been substituted by Gly and the 330 amino acid residue Asp has been substituted by Asn, a double mutant D153H/D330N of *Escherichia coli* alkaline phosphatase (BAP) in which the 153 amino acid residue Asp has been substituted by His and the 330 amino acid residue Asp has been substituted by Asn, or a double mutant K328R/D330N of *Escherichia coli* alkaline phosphatase (BAP) in which the 328 amino acid residue Lys has been substituted by Arg and the 330 amino acid residue Asp has been substituted by Asn.

2 Claims, 18 Drawing Sheets

(56) References Cited

OTHER PUBLICATIONS

Database Geneseq [Online], Oct. 20, 1997, "*E.coli* alkaline phosphatase mutant D153H/Q329A".

B. Jansson, et al, "All individual domains of staphylococcal protein A show Fab binding", FEMS Immunology and Medical Microbiology, Elsevier Science B.V., Amsterdam, NL, vol. 20, No. 1, Jan. 1, 2998, pp. 69-78.

* cited by examiner

2SLN medium, culture supernatant
Vectors: pBIC4, pBIC6, pBIC7, pBIC8
M: molecular weight marker
Sample loading: culture supernatant equivalent to 4 μL of culture liquid TMN medium, culture supernatant
Vectors: pBIC4, pBIC6, pBIC7, pBIC8
M: molecular weight marker
Sample loading: culture supernatant equivalent to 4 μL of culture liquid 2SLN medium, culture supernatant
Vectors: pBIC1, pBIC5, pBIC6, pBIC7, pBIC8
M: molecular weight marker
Sample loading: culture supernatant equivalent to 4 μL of culture liquid TMN medium, culture supernatant
Vectors: pBIC1, pBIC5, pBIC6, pBIC7, pBIC8
M: molecular weight marker
Sample loading: culture supernatant equivalent to 4 μL of culture liquid 2SLN medium, culture supernatant
Vectors: pBIC2, pBIC4, pBIC6, pBIC8
C: Mock (vector only), M: molecular weight marker
Sample loading: culture supernatant equivalent to 4 μL of culture liquid TMN medium, culture supernatant
Vectors: pBIC2, pBIC4, pBIC6, pBIC8
C: Mock (vector only), M: molecular weight marker
Sample loading: culture supernatant equivalent to 4 μL of culture liquid 2SLN medium, culture supernatant
Vectors: pBIC1, pBIC2, pBIC3
C: Mock (vector only), M: molecular weight marker
Sample loading: culture supernatant equivalent to 4 μL of culture liquid TMN medium, culture supernatant
Vectors: pBIC1, pBIC2, pBIC3
C: Mock (vector only), M: molecular weight marker
Sample loading: culture supernatant equivalent to 4 μL of culture liquid 1,5,9: Ni-NTA column unbound fraction 7.5 μL
2,6,10: wash fraction (first repetition) 7.5 μL
3,7,11: purified fraction (first elution, Fr. 1) 1 μL
4,8,12: purified fraction (second elution, Fr. 2) 1 μL
M: molecular weight marker 1,5,9: Ni-NTA column unbound fraction 7.5 μL
2,6,10: wash fraction (first repetition) 7.5 μL
3,7,11: purified fraction (first elution, Fr. 1) 1 μL
4,8,12: purified fraction (second elution, Fr. 2) 1 μL
M: molecular weight marker 1,5: Ni-NTA column unbound fraction 7.5 μL
2,6: wash fraction (first repetition) 7.5 μL
3,7: purified fraction (first elution, Fr. 1) 1 μL
4,8: purified fraction (second elution, Fr. 2) 1 μL
9: BSA 1 μg, M: molecular weight marker 1,5: Ni-NTA column unbound fraction 7.5 μL
2,6: wash fraction (first repetition) 7.5 μL
3,7: purified fraction (first elution, Fr. 1) 1 μL
4,8: purified fraction (second elution, Fr. 2) 1 μL
9: BSA 1 μg, M: molecular weight marker

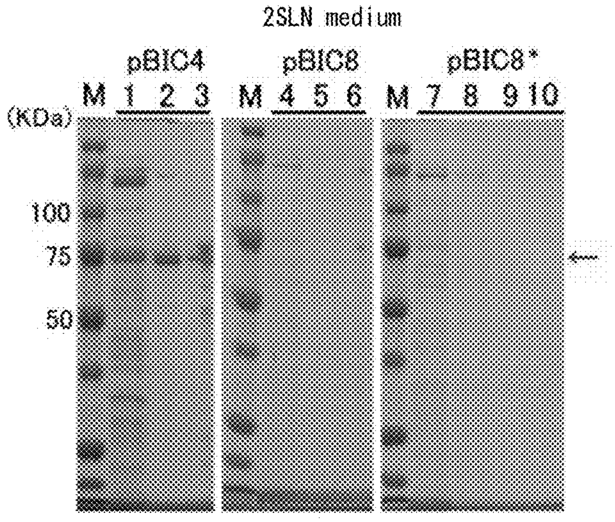

1, 4, 7: Ni-NTA column unbound fraction 10 μL (7.5 μL only for 7)
2, 5, 9: purified fraction (first elution, Fr. 1) 1 μL
3, 6, 10: purified fraction (second elution, Fr. 2) 1 μL
8: Ni-NTA column wash fraction 7.5 μL
M: molecular weight marker
*: results following second purification

FIG. 14

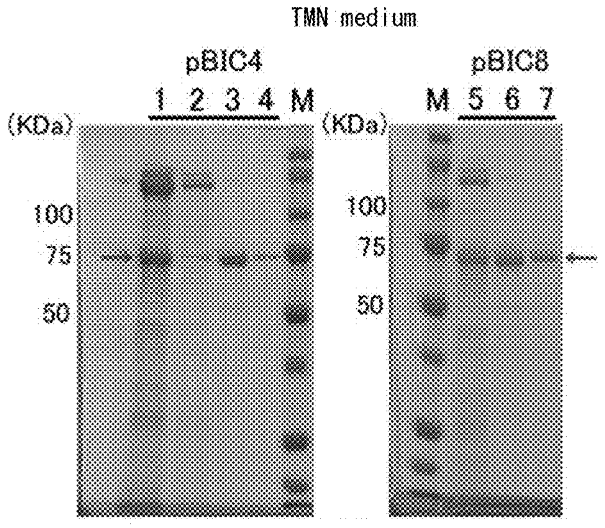

1, 5: Ni-NTA column unbound fraction 7.5 μL (5: 10 μL)
2: Ni-NTA column wash fraction (first repetition) 7.5 μL
3, 6: purified fraction (first elution, Fr. 1) 1 μL
4, 7: purified fraction (second elution, Fr. 2) 1 μL
M: molecular weight marker

FIG. 15

1,5,9: Ni-NTA column unbound fraction 7.5 μL
2,6,10: wash fraction (first repetition) 7.5 μL
3,7,11: purified fraction (first elution, Fr. 1) 1 μL
4,8,12: purified fraction (second elution, Fr. 2) 1 μL
M: molecular weight marker 1,5: Ni-NTA column unbound fraction 7.5 μL
2,6: wash fraction (first repetition) 7.5 μL
3,7: purified fraction (first elution, Fr. 1) 1 μL
4,8: purified fraction (second elution, Fr. 2) 1 μL
M: molecular weight marker 0: Transferrin 10 ng、1: 3 ng、2: 1 ng、3: 300 pg、4: 100 pg、
5: 30 pg、6: 10 pg、7: 3 pg
Exposure time: 3,600 sec., Treatment concentration: 0.5 μg/mL 1: Transferrin 3 ng、2: 1 ng、3: 300 pg、4: 100 pg、
5: 30 pg、6: 10 pg、7: 3 pg
Exposure time: 3,600 sec., Treatment concentration: 0.5 μg/mL 0: Transferrin 10 ng、1: 3 ng、2: 1 ng、3: 300 pg、4: 100 pg、
5: 30 pg、6: 10 pg、7: 3 pg
Exposure time: 3,600 sec., Treatment concentration: 0.5 μg/mL 0: Transferrin 10 ng、1: 3 ng、2: 1 ng、3: 300 pg、4: 100 pg、
5: 30 pg、6: 10 pg、7: 3 pg
Exposure time: 3,600 sec., Treatment concentration: 0.5 μg/mL ADTYKLVINGKTLKGETTTEAVDAATAEKVFKQYANDNGVDGEWTYDDATKT
FTVTEKPEVIDASELTPAVTTYKLVINGKTLKGETTTKAVDAETAEKAFKQYAND
NGVDGVWTYDDATKTFTVTEGGGGSDVDNKFNKEQQNAFWEILHLPNLNEE
QRNGFIQSLKDDPSQSANLLAEAKKLNDAQAPKGGGGSTPEMPVLENRAAQG
DITAPGGARRLTGDQTAALRDSLSDKPAKNIILLIGDGMGDSEITAARNYAEGA
GGFFKGIDALPLTGQYTHYALNKKTGKPDYVTDSAASATAWSTGVKTYNGALG
VDIHEKDHPTILEMAKAAGLATGNVSTAELQGATPAALVAHVTSRKCYGPSAT
SEKCPGNALEKGGKGSITEQLLNARADVTLGGGAKTFAETATAGEWQGKTLRE
QAQARGYQLVSDAASLNSVTEANQQKPLLGLFADGNMPVRWLGPKATYHG
NIDKPAVTCTPNPQRNDSVPTLAQMTDKAIELLSKNEKGFFLQVEGASIDKQN
HAANPCGQIGETVDLDEAVQRALEFAKKEGNTLVIVTADHAHASQIVAPDTKA
PGLTQALNTKDGAVMVMSYGNSEEDSQEHTGSQLRIAAYGPHAANVVGLTD
QTDLFYTMKAALGLKLEGSHHHHHHGGGGSMRHKGS portion: Protein G, portion: Protein A, portion: BAP mutant enzyme,
portion: H6 tag, no underline: linker, other,
portion: mutation site

FIG. 24

ADTYKLVINGKTLKGETTTEAVDAATAEKVFKQYANDNGVDGEWTYDDA
TKTFTVTEKPEVIDASELTPAVTTYKLVINGKTLKGETTTKAVDAETAEKAFK
QYANDNGVDGVWTYDDATKTFTVTEGGGGSDVDNKFNKEQQNAFWEI
LHLPNLNEEQRNGFIQSLKDDPSQSANLLAEAKKLNDAQAPKGGGGSTPE
MPVLENRAAQGDITAPGGARRLTGDQTAALRDSLSDKPAKNIILLIGDGM
GDSEITAARNYAEGAGGFFKGIDALPLTGQYTHYALNKKTGKPDYVTDSA
ASATAWSTGVKTYNGALGVDIHEKDHPTILEMAKAAGLATGNVSTAELQ
HATPAALVAHVTSRKCYGPSATSEKCPGNALEKGGKGSITEQLLNARADV
TLGGGAKTFAETATAGEWQGKTLREQAQARGYQLVSDAASLNSVTEAN
QQKPLLGLFADGNMPVRWLGPKATYHGNIDKPAVTCTPNPQRNDSVPT
LAQMTDKAIELLSKNEKGFFLQVEGASIDKQNHAANPCGQIGETVDLDEA
VQRALEFAKKEGNTLVIVTADHAHASQIVAPDTKAPGLTQALNTKDGAV
MVMSYGNSEEDSQEHTGSQLRIAAYGPHAANVVGLTDQTDLFYTMKAA
LGLKLEGSHHHHHHGGGGSMRHKGS portion: Protein G, portion: Protein A, portion: BAP mutant enzyme,
portion: H6 tag, no underline: linker, other,
portion: mutation site

FIG. 25

ADTYKLVINGKTLKGETTTEAVDAATAEKVFKQYANDNGVDGEWTY
DDATKTFTVTEKPEVIDASELTPAVTTYKLVINGKTLKGETTTKAVDAE
TAEKAFKQYANDNGVDGVWTYDDATKTFTVTEGGGGSDVDNKFN
KEQQNAFWEILHLPNLNEEQRNGFIQSLKDDPSQSANLLAEAKKLN
DAQAPKGGGGSTPEMPVLENRAAQGDITAPGGARRLTGDQTAAL
RDSLSDKPAKNIILLIGDGMGDSEITAARNYAEGAGGFFKGIDALPLT
GQYTHYALNKKTGKPDYVTDSAASATAWSTGVKTYNGALGVDIHEK
DHPTILEMAKAAGLATGNVSTAELQDATPAALVAHVTSRKCYGPSA
TSEKCPGNALEKGGKGSITEQLLNARADVTLGGGAKTFAETATAGE
WQGKTLREQAQARGYQLVSDAASLNSVTEANQQKPLLGLFADGN
MPVRWLGPKATYHGNIDKPAVTCTPNPQRNDSVPTLAQMTDKAIE
LLSKNEKGFFLQVEGASIDRQNHAANPCGQIGETVDLDEAVQRALE
FAKKEGNTLVIVTADHAHASQIVAPDTKAPGLTQALNTKDGAVMV
MSYGNSEEDSQEHTGSQLRIAAYGPHAANVVGLTDQTDLFYTMKA
ALGLKLEGSHHHHHHGGGGSMRHKGS portion: Protein G, portion: Protein A, portion: BAP mutant enzyme,
portion: H6 tag, no underline: linker, other,
portion: mutation site

FIG. 26

ADTPEMPVLENRAAQGDITAPGGARRLTGDQTAALRDSLSDKPAKNIILL
IGDGMGDSEITAARNYAEGAGGFFKGIDALPLTGQYTHYALNKKTGKPD
YVTDSAASATAWSTGVKTYNGALGVDIHEKDHPTILEMAKAAGLATGNV
STAELQDATPAALVAHVTSRKCYGPSATSEKCPGNALEKGGKGSITEQLL
NARADVTLGGGAKTFAETATAGEWQGKTLREQAQARGYQLVSDAASL
NSVTEANQQKPLLGLFADGNMPVRWLGPKATYHGNIDKPAVTCTPNPQ
RNDSVPTLAQMTDKAIELLSKNEKGFFLQVEGASIDRQNHAANPCGQIG
ETVDLDEAVQRALEFAKKEGNTLVIVTADHAHASQIVAPDTKAPGLTQAL
NTKDGAVMVMSYGNSEEDSQEHTGSQLRIAAYGPHAANVVGLTDQTD
LFYTMKAALGLKLEGGGGSDVDNKFNKEQQNAFWEILHLPNLNEEQRN
GFIQSLKDDPSQSANLLAEAKKLNDAQAPKGGGGSTYKLVINGKTLKGET
TTEAVDAATAEKVFKQYANDNGVDGEWTYDDATKTFTVTEKPEVIDASE
LTPAVTTYKLVINGKTLKGETTTKAVDAETAEKAFKQYANDNGVDGVWT
YDDATKTFTVTEGSHHHHHHGGGGSMRHKGS portion: Protein G, portion: Protein A, portion: BAP mutant enzyme,
portion: H6 tag, no underline: linker, other,
portion: mutation site

FIG. 27

FUSION PROTEIN FOR PROTEIN DETECTION, AND METHOD FOR DETECTING PROTEIN

The Sequence Listing associated with this application is filed in electronic format via EFS-Web and is hereby incorporated by reference into the specification in its entirety. The name of the text file containing the Sequence Listing is Sequence Listing. The size of the text file is 36,293 bytes, and the text file was created on Nov. 20, 2017.

TECHNICAL FIELD

The present invention relates to a fusion protein for protein detection, and a method for detecting protein.

BACKGROUND ART

A variety of proteins exist in biological samples, and methods such as ELISA (Enzyme-Linked ImmunoSorbent Assay) are known as methods for detecting and quantifying specific proteins.

ELISA is a method for quantitatively detecting a specific protein such as an antigen contained in a sample, by using an enzyme-labeled antibody and utilizing an antigen-antibody reaction, and is one technique that is widely used in immunological tests and the like. Known forms of ELISA include the direct adsorption method, the sandwich method and the competitive method.

For example, a primary antibody for a target material (antigen) adsorbed to the surface of a solid phase is bound via an antigen-antibody reaction. The unreacted primary antibody is washed away, and an enzyme-labeled secondary antibody is then added and bound via a second antigen-antibody reaction. The unreacted labeled secondary antibody is then washed away, and when a chromogenic substrate is added, a color reaction occurs in proportion to the amount of the antigen. The absorbance of the thus generated colored material is measured using an absorbance meter or the like, and the amount of the antigen can be quantified by using a calibration curve prepared using standard samples of known concentration.

However, in this type of method, a labeled secondary antibody is required which binds specifically to the primary antibody that binds specifically to the target material (antigen), and when a plurality of types of target materials (antigens) are to be detected, a series of labeled secondary antibodies must be prepared to bind specifically to each of the plurality of primary antibodies, meaning the method suffers from poor versatility.

Alkaline phosphatases are well known as enzymes for protein detection, and among such alkaline phosphatases, CIAP (Calf Intestine Alkaline Phosphatase) is widely used. Conventionally, CIAP purified from calf small intestines is widely used, but in recent years, CIAP prepared by gene recombination has also become available commercially. However, the former is expensive to produce, and achieving stable quality is difficult. Further, in the case of the latter, production by expression in yeast or the like is used to reduce the production costs, but excessive glycosylation may occur, meaning problems relating to the background and viscosity and the like frequently occur. Further, although CIAP exhibits high activity, it suffers from poor stability, particularly thermal stability, and therefore maintaining the activity for long periods is difficult, and use of CIAP in gene-related applications which require heating is impossible. Moreover, because the activity decreases when diluted, in actual applications where the CIAP is used for long periods at low concentration, this property of high activity cannot be adequately realized.

BAP (Bacterial Alkaline Phosphatase) exhibits high stability, but because the activity is low, specifically only a few percent of the activity of CIAP, it has hardly been used at all for protein detection.

On the other hand, another method is known which, instead of using a labeled secondary antibody, uses an enzyme-labeled protein G prepared by binding an enzyme such as an alkaline phosphatase and protein G by chemical reaction. Protein G is a protein derived from the cell walls of streptococcal bacteria, and has a property of binding to the IgG of almost all mammals. By using this type of enzyme-labeled protein G, binding is possible with the primary antibodies of many immunity types, and even when a plurality of target materials (antigens) are to be detected, separate antibodies for binding specifically to each target material need not be prepared, thus offering excellent versatility.

However, methods using an enzyme-labeled protein G that has been labeled with an enzyme such as alkaline phosphatase have suffered from problems of low detection sensitivity. Further, thermal stability is also low, and loss of activity during handling may sometimes occur.

Non-Patent Document 1 discloses the preparation of a fusion protein in which a C1 domain of protein G (SpG) is bound to the N-terminal of *Vargula hilgendorfii* luciferase, but the fusion protein had no antibody binding ability, and a protein having a linker GGGGS inserted between the two moieties exhibited similar results.

Non-Patent Document 2 discloses the gene sequence, amino acid sequence, structure, and the function of each domain for protein G.

Non-Patent Document 3 discloses double mutants in which the amino acid residues at specific locations of BAP have been substituted, such as D153G/D330N and D153H/D330N, and examines the activity, stability, optimum pH, substrates, and metal ion affinity and activity of these mutants.

Patent Document 1 discloses mutations in which the amino acid residues at specific locations of BAP have been substituted, including mutants D153G and K328R, and the double mutant V99A/K328R, and discloses applications such as sandwich ELISA and competitive methods.

Patent Document 2 discloses mutations at position 329, position 330, and positions 153/328 of BAP, and discloses the preparation of a fusion protein with an antigen and the conducting of competitive ELISA.

Patent Document 3 discloses mutants of BAP such as K328R, and describes chemical binding to an antibody and ELISA.

PRIOR ART DOCUMENTS

Patent Documents

Patent Document 1: JP 3560972 B
Patent Document 2: JP H09-098780 A
Patent Document 3: JP 2620416 B

Non-Patent Documents

Non-Patent Document 1: Engineering of functional chimeric protein G-*Vargula* luciferase, ANALYTICAL BIOCHEMISTRY, 249(2), pp. 147 to 152 (1997)

Non-Patent Document 2: Expression and purification of a truncated recombinant streptococcal protein G, Biochem J., 267(1), pp. 171 to 177 (1990)

Non-Patent Document 3: Improving *Escherichia coli* Alkaline Phosphatase Efficacy by Additional Mutations inside and outside the Catalytic Pocket., Chembiochem., 2, pp. 517 to 523 (2001)

SUMMARY OF THE INVENTION

Problems to be Solved by the Invention

The present invention has objects of providing a fusion protein for protein detection that exhibits superior versatility, high detection sensitivity and superior stability, and providing a method for detecting a protein using the fusion protein.

Means for Solving the Problems

The present invention provides a fusion protein for protein detection in which are fused: a protein domain including at least one among a C1 domain of protein G, a C2 domain of protein G and a C3 domain of protein G; and a double mutant D153G/D330N of *Escherichia coli* alkaline phosphatase (BAP) in which the amino acid residue Asp at position 153 has been substituted by Gly and the amino acid residue Asp at position 330 has been substituted by Asn, a double mutant D153H/D330N of *Escherichia coli* alkaline phosphatase (BAP) in which the amino acid residue Asp at position 153 has been substituted by His and the amino acid residue Asp at position 330 has been substituted by Asn, or a double mutant K328R/D330N of *Escherichia coli* alkaline phosphatase (BAP) in which the amino acid residue Lys at position 328 has been substituted by Arg and the amino acid residue Asp at position 330 has been substituted by Asn.

Further, in the above fusion protein for protein detection, the protein domain is preferably a domain in which a B domain of protein A, a C2 domain of protein G and a C3 domain of protein G are linked.

Furthermore, the present invention also provides a method for detecting a protein, the method comprising binding, either directly or indirectly, the fusion protein for protein detection described above and a protein that exists within a target material, and detecting the alkaline phosphatase portion of the bound fusion protein for protein detection as a labeling portion.

Advantages of the Invention

By fusing a protein domain including at least one among a C1 domain of protein G, a C2 domain of protein G and a C3 domain of protein G, and a double mutant D153G/D330N, D153H/D330N or K328R/D330N of *Escherichia coli* alkaline phosphatase (BAP), the present invention is able to provide a fusion protein for protein detection that exhibits superior versatility, high detection sensitivity and superior stability, as well as providing a method for detecting a protein using the fusion protein.

BRIEF DESCRIPTION OF THE DRAWINGS

FIG. 14 is a diagram illustrating the purification of an expressed protein (pG-K328R/D330N (pG binding site: N-terminal)) using a Ni-NTA column in Example 2 (vectors: pBIC4, pBIC8, medium: 2SLN, the arrow indicates the electrophoretic position of pG-K328R/D330N).

FIG. 15 is a diagram illustrating the purification of an expressed protein (pG-K328R/D330N (pG binding site: N-terminal)) using a Ni-NTA column in Example 2 (vectors:

pBIC4, pBIC8, medium: TMN, the arrow indicates the electrophoretic position of pG-K328R/D330N).

Figure 16:
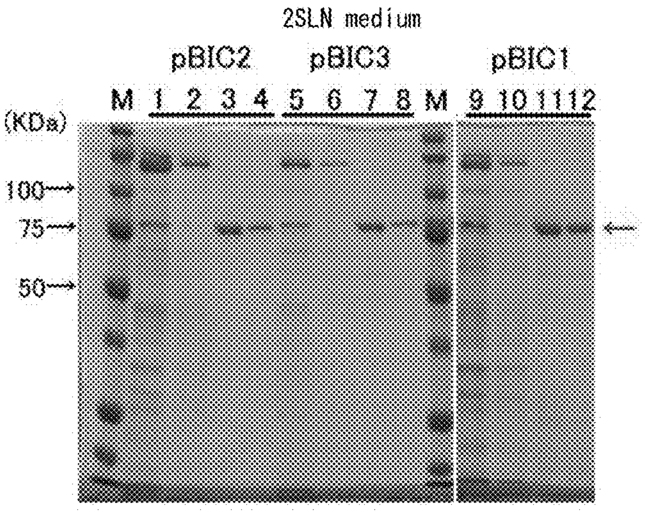

FIG. 16 is a diagram illustrating the purification of an expressed protein (pG-K328R/D330N (pG binding site: C-terminal)) using a Ni-NTA column in Example 2 (vectors: pBIC2, pBIC3, pBIC1, medium: 2SLN, the arrow indicates the electrophoretic position of pG-K328R/D330N).

Figure 17:
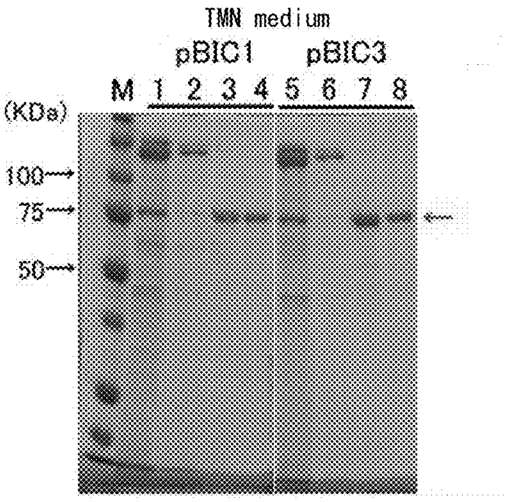

FIG. 17 is a diagram illustrating the purification of an expressed protein (pG-K328R/D330N (pG binding site: C-terminal)) using a Ni-NTA column in Example 2 (vectors: pBIC1, pBIC3, medium: TMN, the arrow indicates the electrophoretic position of pG-K328R/D330N).

Figure 18:
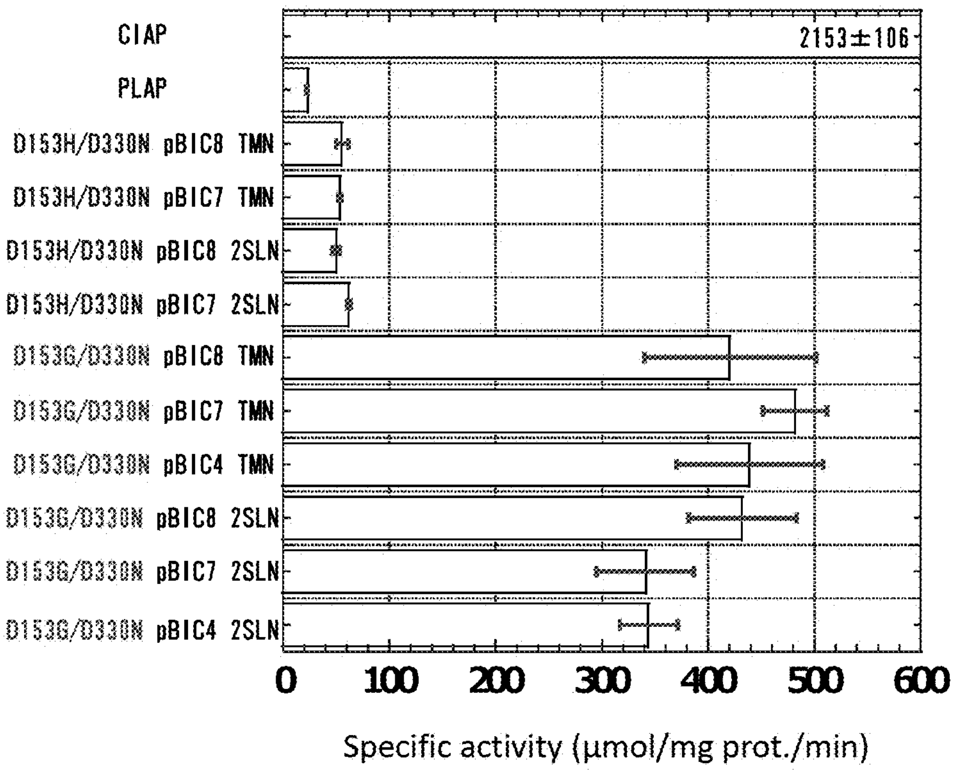

FIG. 18 is a diagram illustrating the ALP activity of purified samples (Fr. 1) of pG-D153G/D330N and pG-D153H/D330N in Example 3 (measurements performed at 45° C., numerical values in the diagram indicate mean±standard deviation across 9 measurements).

Figure 19:
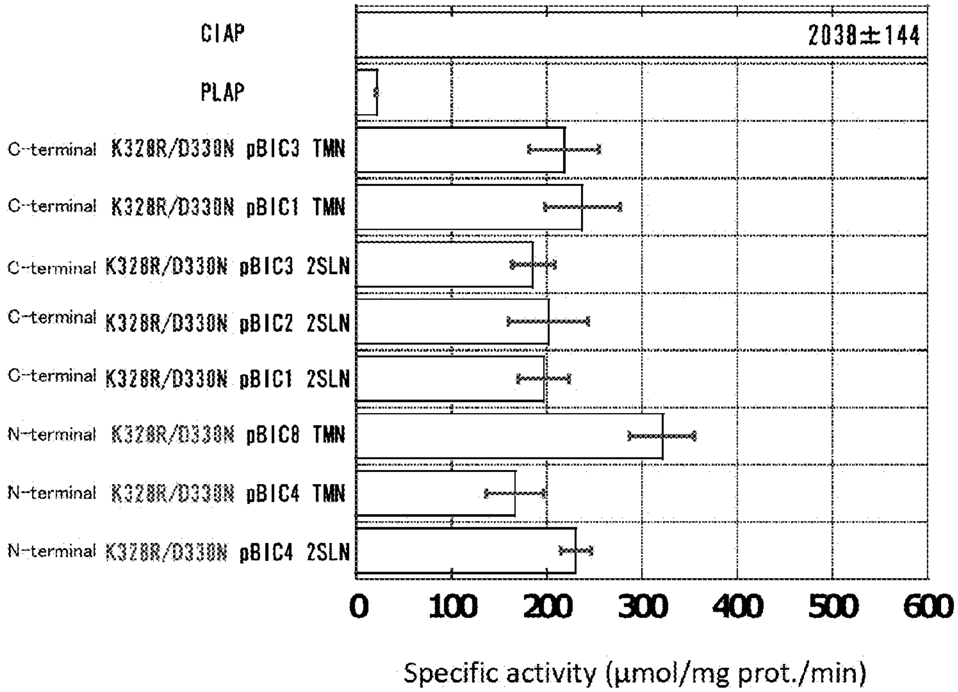

FIG. 19 is a diagram illustrating the ALP activity of purified samples (Fr. 1) of pG-K328R/D330N in Example 3 (measurements performed at 45° C., numerical values in the diagram indicate mean±standard deviation across 9 measurements).

Figure 20:
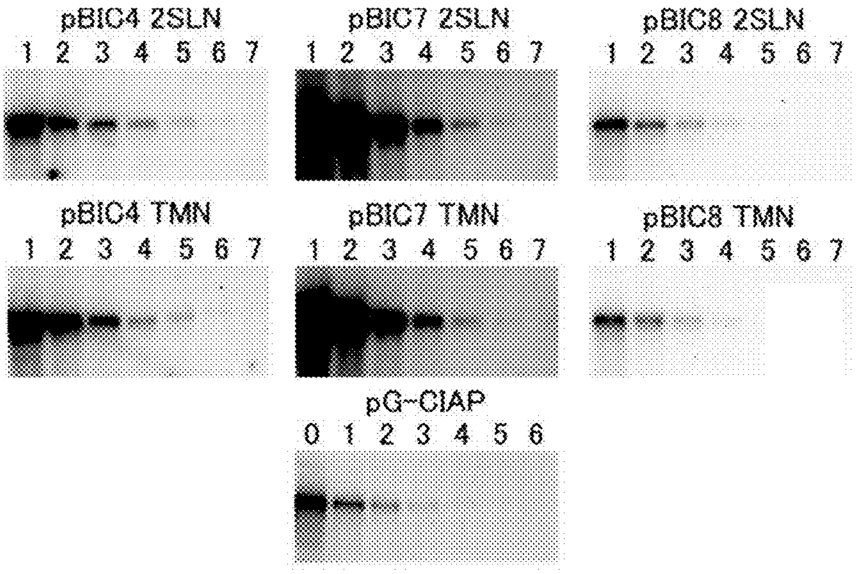

FIG. 20 is a diagram illustrating Western blot results for pG-D153G/D330N (pG binding site: N-terminal) in Example 3.

Figure 21:
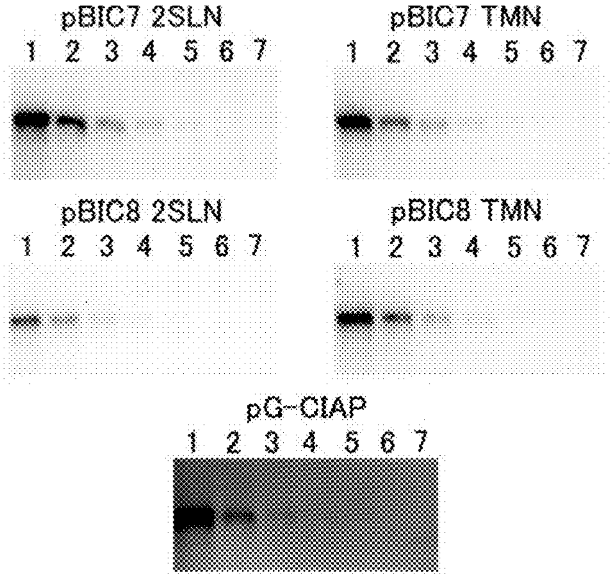

FIG. 21 is a diagram illustrating Western blot results for pG-D153H/D330N (pG binding site: N-terminal) in Example 3.

Figure 22:
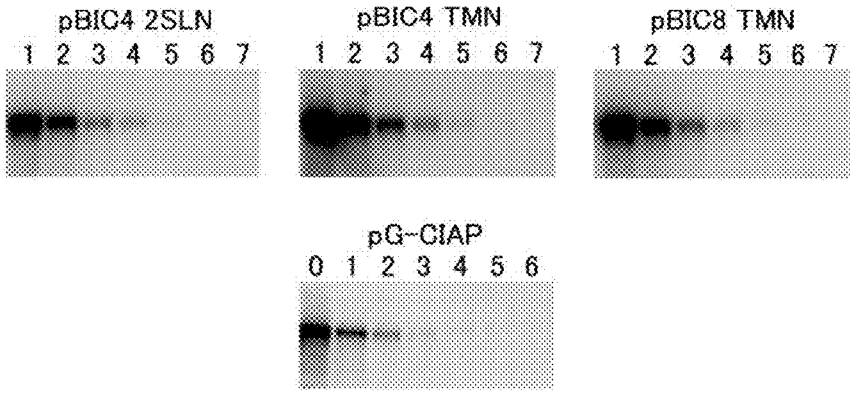

FIG. 22 is a diagram illustrating Western blot results for pG-K328R/D330N (pG binding site: N-terminal) in Example 3.

Figure 23:
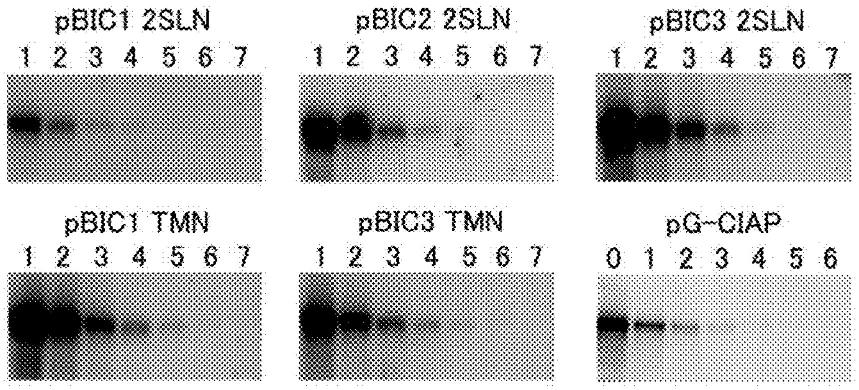

FIG. 23 is a diagram illustrating Western blot results for pG-K328R/D330N (pG binding site: C-terminal) in Example 3.

FIG. 24 is a diagram illustrating the amino acid sequence of a pG-BAP mutant (D153G/D330N).

FIG. 25 is a diagram illustrating the amino acid sequence of a pG-BAP mutant (D153H/D330N).

FIG. 26 is a diagram illustrating the amino acid sequence of a pG-BAP mutant (K328R/D330N (pG binding site: N-terminal)).

FIG. 27 is a diagram illustrating the amino acid sequence of a pG-BAP mutant (K328R/D330N (pG binding site: C-terminal)).

Figure 28:
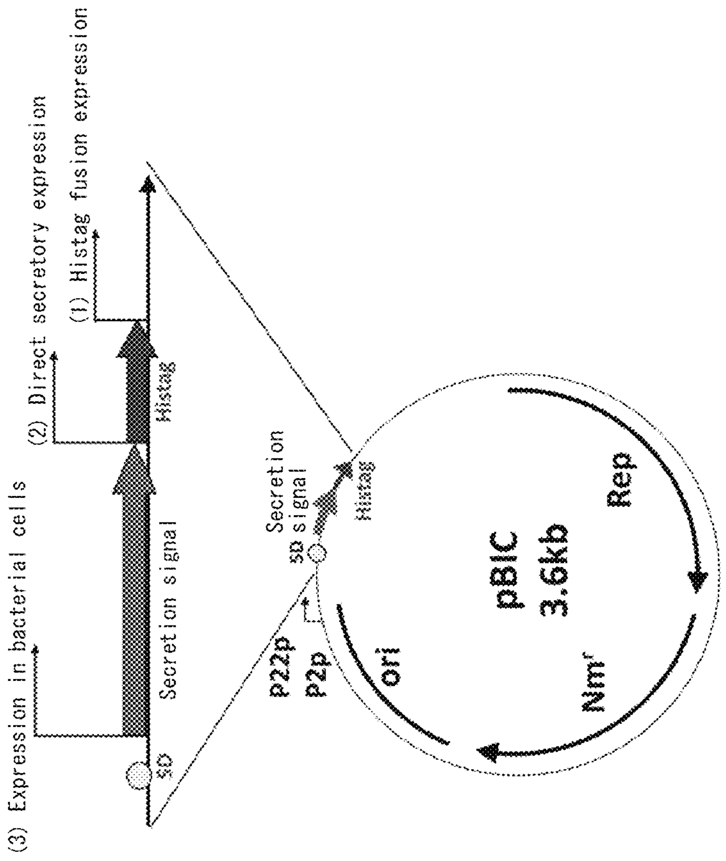

FIG. 28 is a diagram illustrating a pBIC vector map (the gene was introduced directly downstream of a secretion signal. Promoter: *B. choshinensis*-derived P22, P2 protein gene 5' sequence, Rep: protein associated with plasmid self replication, Ori: origin of plasmid replication, Nmr: neomycin resistance gene).

EMBODIMENTS FOR CARRYING OUT THE INVENTION

Embodiments of the present invention are described below. These embodiments are merely examples of implementing the present invention, and the present invention is in no way limited by these embodiments.

A fusion protein for protein detection according to an embodiment of the present invention is a protein in which a protein domain including at least one among a C1 domain of protein G, a C2 domain of protein G and a C3 domain of protein G, and a double mutant D153G/D330N, D153H/D330N or K328R/D330N of *Escherichia coli* alkaline phosphatase (BAP) are fused.

The inventors of the present invention focused their attention on protein G as the protein domain to be bound either directly or indirectly to the protein that represents the detection target material. Protein G is a protein derived from the cell walls of streptococcal bacteria, and has a property of binding to the IgG of almost all mammals. The inventors investigated whether or not this protein G could be labeled with an alkaline phosphatase and used instead of a labeled secondary antibody or the like.

Furthermore, in order to prepare an alkaline phosphatase as a labeling enzyme that contributes to improved detection sensitivity and stability, the inventors of the present invention focused their attention on the contribution to the enzyme activity of the amino acid residues at position 153 or position 328 of *Escherichia coli* alkaline phosphatase (BAP), and the contribution to the enzyme stability of the amino acid residue at position 330, and consequently selected double mutants D153G/D330N, D153H/D330N and K328R/D330N of *Escherichia coli* alkaline phosphatase (BAP). The BAP double mutants D153G/D330N and D153H/D330N have higher stability than the currently widely used CIAP, and have higher activity than BAP (wild type).

Among these BAP double mutants, D153G/D330N is a mutant in which the amino acid residue Asp at position 153 of BAP has been substituted by Gly and the amino acid residue Asp at position 330 has been substituted by Asn, D153H/D330N is a mutant in which the amino acid residue Asp at position 153 of BAP has been substituted by His and the amino acid residue Asp at position 330 has been substituted by Asn, and K328R/D330N is a mutant in which the amino acid residue Lys at position 328 of BAP has been substituted by Arg and the amino acid residue Asp at position 330 has been substituted by Asn.

As a result of intensive investigations, the inventors of the present invention discovered that by fusing a protein domain including at least one among a C1 domain of protein G, a C2 domain of protein G and a C3 domain of protein G, and a BAP double mutant D153G/D330N, D153H/D330N or K328R/D330N, a fusion protein for protein detection could be obtained that exhibits superior versatility, high detection sensitivity and superior stability.

There are no particular limitations on the protein domain, provided it includes at least one protein G IgG-binding domain among a C1 domain, C2 domain and C3 domain, but in terms of factors such as suppressing desorption from the antibody, a protein domain in which a C2 domain of protein G and a C3 domain of protein G are linked is preferable. Further, in terms of factors such as enhancing the reactivity of protein G to antibodies and the like, the protein domain preferably includes at least one among an E domain of protein A, a D domain of protein A, an A domain of protein A, a B domain of protein A and a C domain of protein A, and more preferably includes a B domain of protein A. A protein domain in which a B domain of protein A, a C2 domain of protein G and a C3 domain of protein G are linked is particularly desirable.

The C2 domain of protein G may be fused at either the C-terminal side or the N-terminal side of the fusion alkaline phosphatase. In terms of ease of expression and the like, the C2 domain of protein G is preferably fused at the N-terminal side of the fusion alkaline phosphatase.

The fusion protein for protein detection according to the present invention may also have a tag such as a His tag, which is a type of tag peptide composed of about six linked histidine (His) residues.

Figure 1:
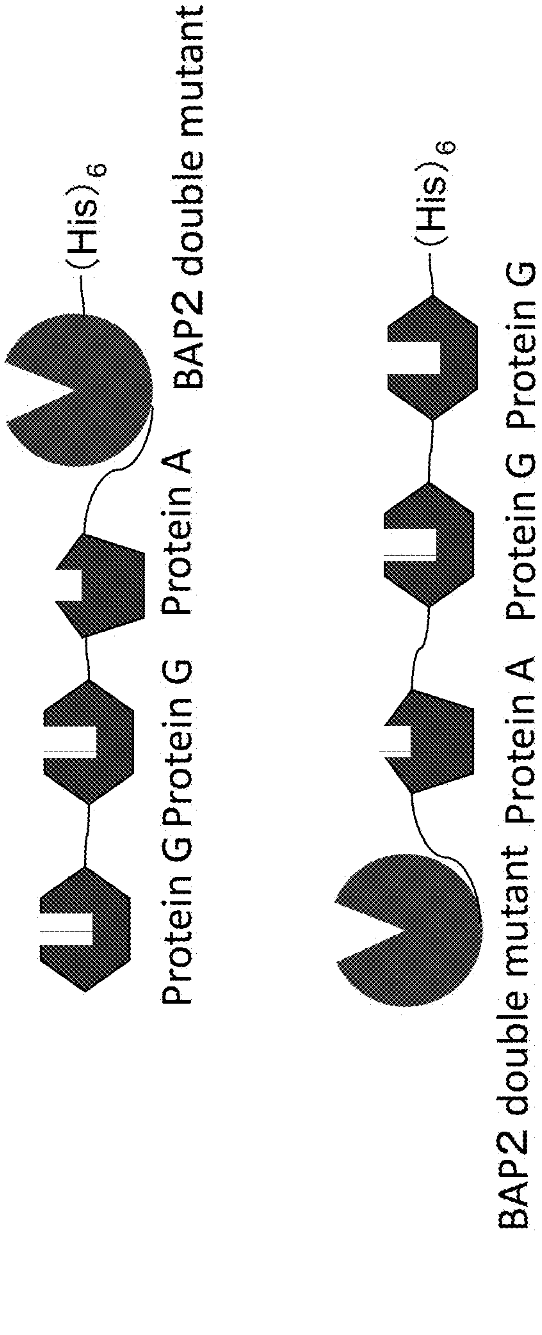
FIG. 1 is a schematic view illustrating structures of examples of the fusion protein for protein detection according to embodiments of the present invention.

FIG. 1 is a diagram schematically illustrating structures of examples of the fusion protein for protein detection according to embodiments of the present invention. Examples of the fusion protein for protein detection according to embodiments of the present invention include a structure in which a B domain of protein A, a C2 domain of protein G and a C3 domain of protein G are bound at the N-terminal side of a BAP double mutant D153G/D330N, D153H/D330N or K328R/D330N, and a His tag is added at the C-terminal side of the BAP double mutant, and a structure in which a B domain of protein A, a C2 domain of protein G and a C3 domain of protein G are bound at the C-terminal side of a BAP double mutant D153G/D330N, D153H/D330N or K328R/D330N, and a His tag is added at the C-terminal side of the protein G domain.

A fusion protein for protein detection according to an embodiment of the present invention can be obtained using genetic engineering techniques, by expressing a fusion protein in which a protein domain including at least one among a C1 domain of protein G, a C2 domain of protein G and a C3 domain of protein G, and a BAP double mutant D153G/D330N, D153H/D330N or K328R/D330N have been fused together. Further, at this time, a tag such as a His tag may also be added at either the N-terminal side or the C-terminal side of a protein G domain or the BAP double mutant.

Purification of the fusion protein can be performed by gel permeation chromatography or immobilized metal ion affinity chromatography or the like, utilizing the purification peptide tag (for example, a (His)6-tag (hexahistidine tag)) that has been added at the N-terminal or C-terminal.

Confirmation of the amino acid sequence of the fusion protein can be achieved by using a DNA sequencer to confirm the gene sequence of a plasmid vector encoding the protein. Confirmation of the purity of the protein can be made by SDS-PAGE or the like.

By using the fusion protein for protein detection according to an embodiment of the present invention, primary antibodies of almost all types of animals can be detected. The detection sensitivity of the fusion protein for protein detection according to an embodiment of the present invention is higher than that of conventional labeled protein G, and the stability is also superior. Furthermore, the detection sensitivity is similar or superior to that of conventional labeled secondary antibodies, and the versatility is high. By using the fusion protein for protein detection according to an embodiment of the present invention, binding is possible to the (primary) antibodies of many immunity types, and a secondary antibody need not to be prepared for each immunity type, meaning versatility is excellent.

This fusion protein for protein detection is a bacteria-derived protein, suffers no problems of post-translational modification, and can be prepared using a microbial expression system. Further, if a secretory expression system is used, the fusion protein can be produced very efficiently. Production can be achieved at low cost compared with the case where an animal-derived protein is extracted and purified, or the case where an animal-derived protein is produced by expression in animal cells.

Animal-derived CIAP or the like includes sugar chains. It is said that these sugar chains are one of the causes of adhesion to measuring containers and membranes and the like, and they also produce a high background. However, in BAP double mutants, because none of this glycosylation that can cause a high background exists, the types of background problems and handling problems and the like due to high viscosity observed for animal-derived enzymes are unlikely.

The enzyme portion exhibits higher activity than BAP and superior stability than CIAP, and has some resistance even at high temperatures, and can therefore also be applied to sensitivity improvements in gene detection (hybridization) and the like that requires high-temperature processes. Further, there is a possibility that proteins can be detected with higher sensitivity than existing pG-CIAP.

Method of Detecting Protein

The method of detecting protein according to an embodiment of the present invention comprises binding, either directly or indirectly, the fusion protein for protein detection described above and a protein that exists within a target material, and detecting the alkaline phosphatase portion of the bound fusion protein for protein detection as a labeling portion.

The fusion protein for protein detection and the method for detecting a protein according to embodiments of the present invention can be used in fundamental research fields such as Western blot analysis, ELISA, immunoprecipitation and immunohistochemistry (immunostaining), and also in fields such as pathological examination.

EXAMPLES

A more detailed description of the present invention is presented below based on a series of examples and comparative examples, but the present invention is in no way limited by the following examples. In the following examples, “room temperature” means 20 to 25° C.

Example 1

An expression vector was constructed by introducing a gene fragment of a pG-BAP mutant into a *Brevibacillus* expression vector. The constructed expression vector was subjected to transformation and culturing for a prescribed time, the culture supernatant and the bacterial cells were separated, and the amount of the target protein contained in the culture supernatant was confirmed.

Materials and Experimental Method

1. Expression Vector (Plasmid)

In secretory expression using *Brevibacillus*, there is a possibility that the optimum protein synthesis rate and the secretion signal may differ for each target protein. Accordingly, a total of eight types of expression vectors, composed of combinations of two types of promoters (pBIC1, pBIC2, pBIC3, pBIC4: P22 promoter (SEQ ID NO: 9), and pBIC5, pBIC6, pBIC7, pBIC8: P2 promoter (SEQ ID NO: 10)) and four types of secretion signals (pBIC1, pBIC5: SEQ ID NO: 11, pBIC2, pBIC6: SEQ ID NO: 12, pBIC3, pBIC7: SEQ ID NO: 13, and pBIC4, pBIC8: SEQ ID NO: 14), were used (see FIG. 28).

Vectors used: pBIC1 to PBIC8 (provided by Higeta Shoyu Co., Ltd.).

2. Expression Vector Construction

In order to introduce gene fragments of each of the pG-BAP mutants (pG-D153G/D330N, pG-D153H/D330N and pG-K328R/D330N) into the expression vector, the BIC method (*Brevibacillus* in vivo Cloning) was used, which is a simple plasmid construction method that does not require an enzyme treatment. In the BIC method, DNA in which a sequence of 15 bp homologous to the two terminals of the linearized expression vector has been added to both terminals of the gene which encodes the target protein is mixed with the vector and introduced into competent cells. A recombination reaction of the homologous sequences occurs within the bacterial cells, forming an expression plasmid. Those vectors among the eight vectors for which vector construction was possible, and for which a vector for expression of the target protein was able to be obtained were subjected to the following expression experiment.

3. Host for Secretory Expression

*Brevibacillus choshinensis* HPD31-SP3 strain (provided by Higeta Shoyu Co., Ltd.).

4. *Brevibacillus* Transformation (DNA Introduction)

The *Brevibacillus choshinensis* HPD31-SP3 strain was subjected to shaking culture at 37° C. in an MT medium (TM medium containing 20 mM of added $MgCl_2$ (see Table 1)) until the logarithmic growth phase, and the bacterial cells were collected by centrifugal separation. Next, the bacterial cells were suspended in 50 mM Tris-HCl (pH 7.5), and following collection by centrifugal separation, were again suspended in 50 mM Tris-HCl (pH 8.5) and subjected to shaking for 60 minutes at 37° C. Subsequently, 500 μL of the shaken suspension was subjected to centrifugal separation to collect the bacterial cells, a mixed solution containing 5 μL of a 2 ng/μL expression vector DNA solution and 50 μL of a 0.5 M $NaSO_3$/70 mM phosphate buffer (pH 6.3) was added and suspended, and after standing for 5 minutes, 150 μL of 40% PEG6000/70 mM phosphate buffer (pH 6.3) was added, and the resulting mixture was stirred and suspended using a vortex stirrer.

TABLE 1

| TM medium | |
|---|---|
| Glucose | 10 g/L |
| Phytone Peptone | 10 g/L |
| Elrich bonito extract | 5 g/L |
| Powdered yeast extract S | 2 g/L |
| $FeSO_4 \cdot 7H_2O$ | 10 mg/L |
| $MnSO_4 \cdot 4H_2O$ | 10 mg/L |
| $ZnSO_4 \cdot 7H_2O$ | 1 mg/L |
| (adjusted to pH 7.0) | |

5. Selection of Transformant

The transformed bacterial cells were collected by centrifugal separation, suspended in 1 mL of TM medium, and shaken for 60 minutes at 37° C. Subsequently, the transformant was selected by smearing the suspension on TMN (an agar medium in which 10 μg/mL of neomycin has been added to TM medium) and cultivating for 30 minutes at 37° C.

6. Cultivation of Transformant

Three mL of TMN medium, and 2SLN medium (2SL medium (see Table 2) containing 50 μg/mL of added neomycin) were injected into a test tube of diameter 16 mm, and the single colony selected in the section described above was inoculated in the mixed media. Shaking cultivation was performed for 48 hours at 30° C. and 120 rpm.

TABLE 2

| 2SL medium | |
|---|---|
| Glucose | 20 g/L |
| Bacto Soytone | 40 g/L |
| Bacto Yeast Extract | 5 g/L |
| $MgSO_4 \cdot 2H_2O$ | 100 mg/L |
| $FeSO_4 \cdot 7H_2O$ | 10 mg/L |
| $MnSO_4 \cdot 4H_2O$ | 10 mg/L |
| $ZnSO_4 \cdot 7H_2O$ | 1 mg/L |

7. Separation of Bacterial Cells and Culture Supernatant

The bacterial cells and the culture supernatant were separated by centrifugal separation (5,000 g, 5 minutes). The culture supernatant was then filtered through a 0.22 μm filtration/sterilization filter to remove residual bacterial cells.

8. Expression Confirmation

An equal volume of 2× sample buffer was added to the culture supernatant, and following modification for 5 minutes at 100° C., the sample was submitted to SDS-PAGE, and the sizes of the produced proteins in each sample were confirmed, and the amounts of expression production were estimated and compared.

Results

1. Confirmation of Expression in Bacterial Cells and Culture Supernatant pG-D153G/D330N (pG-binding site: N-terminal)

Figure 2:
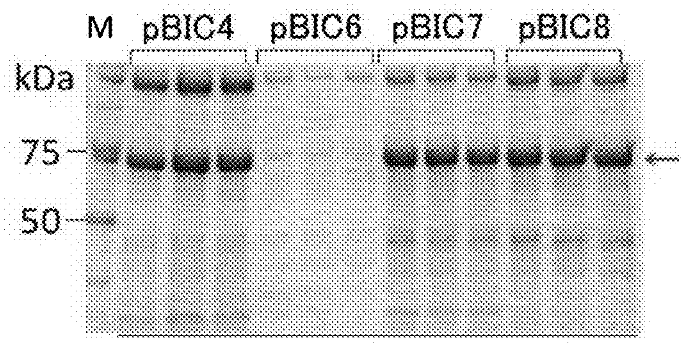
FIG. 2 is a diagram illustrating the expression level of pG-D153G/D330N (pG binding site: N-terminal) in Example 1 (2SLN medium, culture supernatant cultivated at 3 mL scale, 3 lines, the arrow indicates the electrophoretic position of pG-D153G/D330N).
Figure 3:
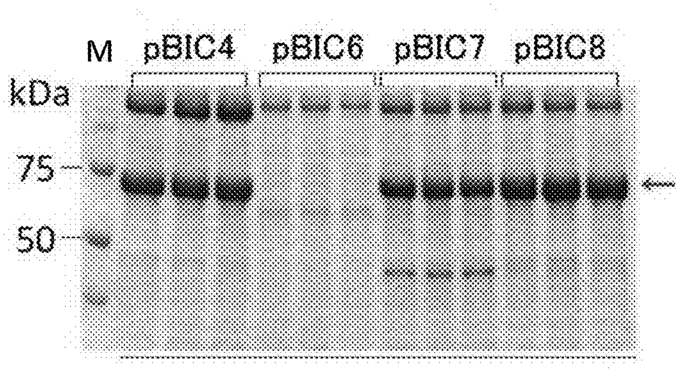
FIG. 3 is a diagram illustrating the expression level of pG-D153G/D330N (pG binding site: N-terminal) in Example 1 (TMN medium, culture supernatant cultivated at 3 mL scale, 3 lines, the arrow indicates the electrophoretic position of pG-D153G/D330N).

In the case of pG-D153G/D330N, among the total of eight combinations of the two types of vector and the four types of signal peptides, expression experiments were performed for the four combinations for which an expression plasmid was able to be obtained. In the case of the 2SLN medium (culture supernatant), a high level of expression was confirmed for pBIC4, pBIC7 and pBIC8, and there was almost no difference in the lines, indicating stable expression. In the TMN medium, with the exception of an increase in the expression level compared with the 2SLN medium, similar tendencies were observed, and it was clear that for pBIC6, almost none of the target protein was produced in either medium (FIGS. 2 and 3). The amino acid sequence of pG-D153G/D330N is shown in FIG. 24 and SEQ ID NO: 1, and the DNA sequence is shown in SEQ ID NO: 2.

pG-D153H/D330N (pG-binding site: N-terminal)

Figure 4:
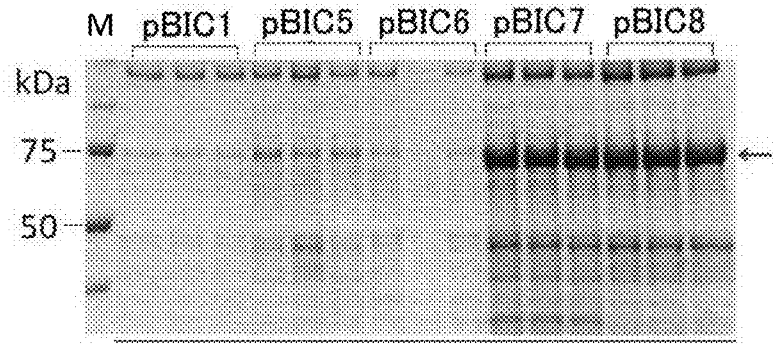
FIG. 4 is a diagram illustrating the expression level of pG-D153H/D330N (pG binding site: N-terminal) in Example 1 (2SLN medium, culture supernatant cultivated at 3 mL scale, 3 lines, the arrow indicates the electrophoretic position of pG-D153H/D330N).
Figure 5:
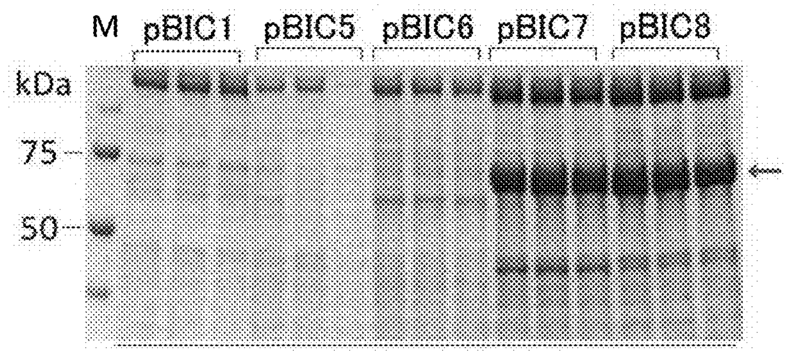
FIG. 5 is a diagram illustrating the expression level of pG-D153H/D330N (pG binding site: N-terminal) in Example 1 (TMN medium, culture supernatant cultivated at 3 mL scale, 3 lines, the arrow indicates the electrophoretic position of pG-D153H/D330N).

In the case of pG-D153H/D330N, for which five expression vectors were obtained, high expression levels were confirmed in both the 2SLN medium and the TMN medium for pBIC7 and pBIC8, and the expression level tended to be higher in the TMN medium. The fact that no variation in the lines was observed indicates stable expression was possible. In the case of pBIC1, pBIC5 and pBIC 6, almost no expression of pG-D153H/D330N was observed (FIGS. 4 and 5). The amino acid sequence of pG-D153H/D330N is shown in FIG. 25 and SEQ ID NO: 3, and the DNA sequence is shown in SEQ ID NO: 4.

For both pG-D153G/D330N and pG-D153H/D330N, SDS-PAGE band intensities for the expression systems having the highest expression levels suggest that production amounts at the g/L level can be anticipated.

pG-K328R/D330N (pG-binding site: N-terminal)

Figure 6:
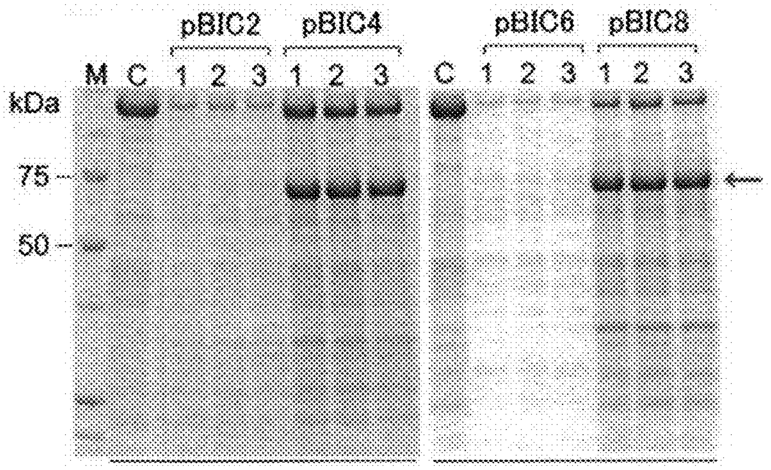
FIG. 6 is a diagram illustrating the expression level of pG-K328R/D330N (pG binding site: N-terminal) in Example 1 (2SLN medium, culture supernatant cultivated at 3 mL scale, 3 lines, the arrow indicates the electrophoretic position of pG-K328R/D330N).
Figure 7:
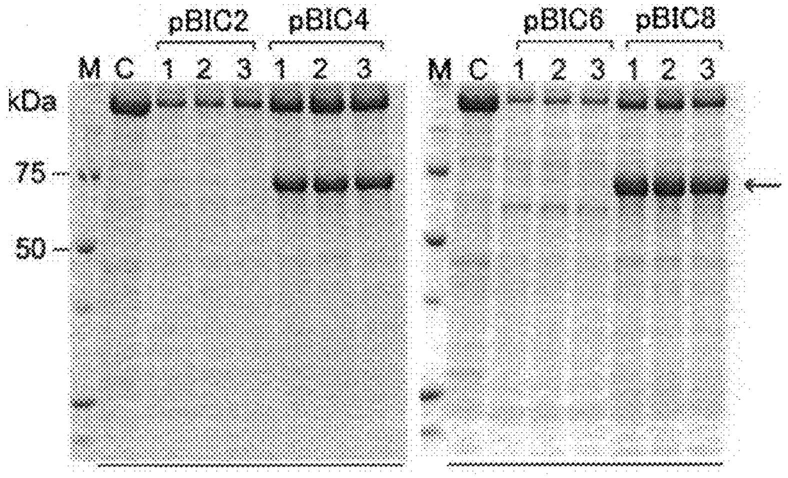
FIG. 7 is a diagram illustrating the expression level of pG-K328R/D330N (pG binding site: N-terminal) in Example 1 (TMN medium, culture supernatant cultivated at 3 mL scale, 3 lines, the arrow indicates the electrophoretic position of pG-K328R/D330N).

In the case of pG-K328R/D330N (pG-binding site: N-terminal), of the four obtained expression vectors, pBIC4 and pBIC8 yielded production of the target protein. Both vectors exhibited minimal variation in the lines, indicating stable expression, and comparing the media, a slightly higher expression level tended to be observed for pBIC8 in the TMN medium (FIGS. 6 and 7). The amino acid sequence of pG-K328R/D330N (pG-binding site: N-terminal) is shown in FIG. 26 and SEQ ID NO: 5, and the DNA sequence is shown in SEQ ID NO: 6.

pG-K328R/D330N (pG-binding site: C-terminal)

Figure 8:
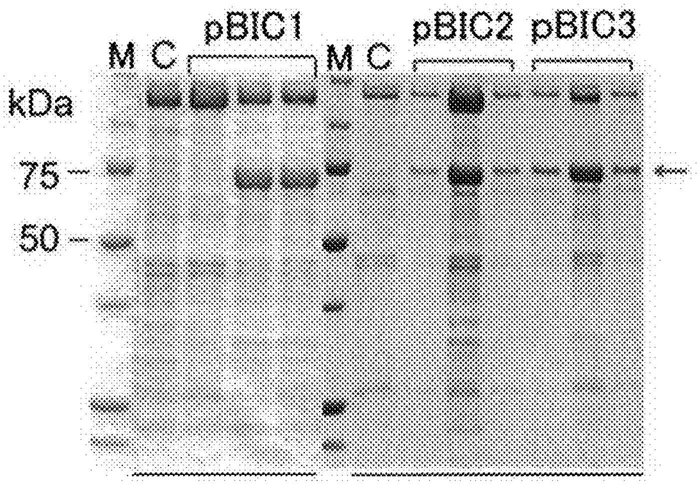
FIG. 8 is a diagram illustrating the expression level of pG-K328R/D330N (pG binding site: C-terminal) in Example 1 (2SLN medium, culture supernatant cultivated at 3 mL scale, 3 lines, the arrow indicates the electrophoretic position of pG-K328R/D330N).
Figure 9:
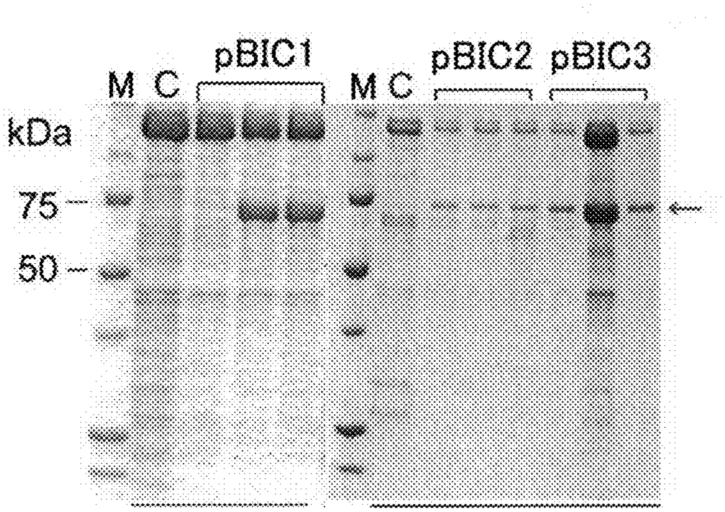
FIG. 9 is a diagram illustrating the expression level of pG-K328R/D330N (pG binding site: C-terminal) in Example 1 (TMN medium, culture supernatant cultivated at 3 mL scale, 3 lines, the arrow indicates the electrophoretic position of pG-K328R/D330N).

In the case of the K328R/D330N in which pG was bound at the C-terminal, of the three obtained expression vectors (pBIC1, pBIC2, pBIC3), production of the target protein was confirmed in all of the vectors in the case of the 2SLN medium, but in the TMN medium, the amount of production for pBIC2 was markedly lower. Comparing the structure having pG bound at the N-terminal with that having pG bound at the C-terminal, no significant difference in band intensity for the target protein was observed for those expression systems in which production was observed. However, in the C-terminal bound structure, similar production levels were not observed in the 3 lines, indicating that, compared with the N-terminal bound structure, the protein expression may lack stability (FIGS. 8 and 9). The amino acid sequence of pG-K328R/D330N (pG-binding site: C terminal) is shown in FIG. 27 and SEQ ID NO: 7, and the DNA sequence is shown in SEQ ID NO: 8.

Example 2

As mentioned above, a histidine tag (H6 tag) can be added to the C-terminal of a BAP mutant expressed in *Brevibacillus*, and purification then performed comparatively easily using a Ni-NTA column. In this example, a purified sample was obtained from the culture supernatant.

Materials and Experimental Method

1. Purification of Target Protein

A simple purification was performed using a His SpinTrap Kit (28-9321-71/GE Healthcare), which is a type of Ni-NTA column. The purification operation was performed in accordance with the included instruction manual, using 300 to 600 μL of the culture supernatant, and the imidazole concentration of the culture supernatant at the time of column binding and the imidazole concentration of the binding (wash) buffer set to 40 mM, and the imidazole concentration of the elution buffer set to 500 mM. Further, following addition of the culture supernatant to the column, washing was performed three times, and then enzyme elution was performed twice, with the eluted fractions termed “fractions 1 and 2” (Fr. 1 and Fr. 2).

2. Desalting and Concentration

The purified mutant enzyme solution contained a high concentration of imidazole, and because the results of preliminary testing revealed that this imidazole had an adverse effect on the enzyme activity, desalting to remove the imidazole and a solvent substitution into a storage buffer (described below) were performed. These operations were performed using a gel filtration method (Zeba Desalt Spin Columns, 89890/Thermo Scientific) or an ultrafiltration method (Amicon Ultra Centrifugal Filters, 10K membrane, UFC501024/Millipore). The purified sample obtained upon solvent substitution was concentrated about 4- to 5-fold by ultrafiltration (as above) and then stored at 4° C.

Storage buffer: 100 mM Tris-HCl (pH 8.0), 100 mM NaCl, 1 mM $MgCl_2$, 20 μM $ZnCl_2$

3. Purity Confirmation and Protein Quantification

The purity of the obtained purified sample was confirmed using an SDS-PAGE method. The gel used was a Mini PROTEAN (a registered trademark) TGX (trademark) precast gel (456-1036/Bio-Rad). Following electrophoresis, the gel was washed with purified water and the protein bands were visualized by CBB staining (Quick-CBB PLUS, 178-00551/Wako Pure Chemical Industries).

Protein quantification was performed using the Micro BCA method (BCA Protein Assay Reagent Kit, 23227/Thermo Scientific). A prescribed amount of the purified sample and an equal amount of the detection reagent were mixed, the mixture was treated at 60° C. for one hour, and following cooling, OD562 was measured. A calibration curve was prepared using BSA (Bovine Serum Albumin) as a standard protein, thus enabling determination of the amount of protein.

Results

1. Purification by Ni-NTA Column pG-D153G/D330N (pG-binding site: N-terminal)

Figure 10:
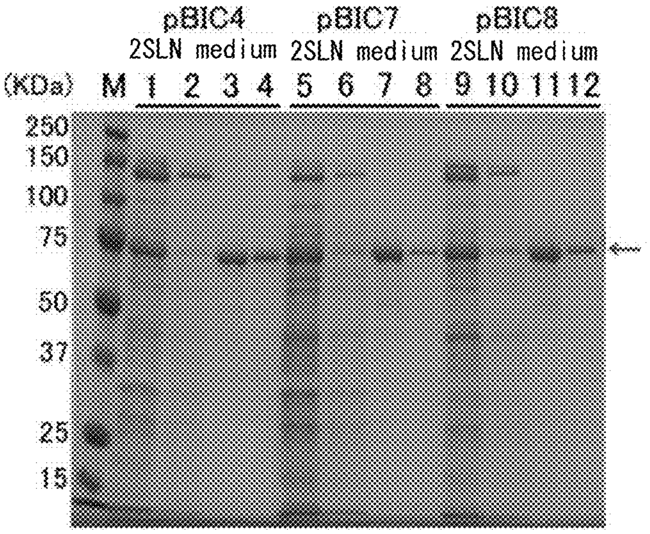
FIG. 10 is a diagram illustrating the purification of an expressed protein (pG-D153G/D330N) using a Ni-NTA column in Example 2 (vectors: pBIC4, pBIC7, pBIC8, medium: 2SLN, the arrow indicates the electrophoretic position of pG-D153G/D330N).
Figure 11:
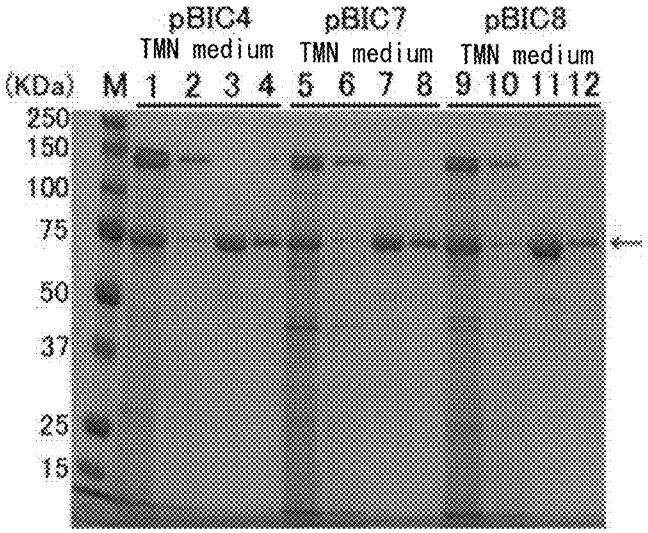
FIG. 11 is a diagram illustrating the purification of an expressed protein (pG-D153G/D330N) using a Ni-NTA column in Example 2 (vectors: pBIC4, pBIC7, pBIC8, medium: TMN, the arrow indicates the electrophoretic position of pG-D153G/D330N).

For each combination of a pG-D153G/D330N vector and medium that yielded a high expression level in the expression experiments, a simple purification was performed from the culture supernatant using a Ni-NTA column (FIGS. 10 and 11). For each of the tested combinations (pBIC4, pBIC7, pBIC8), impurities were almost entirely removed from the purified fraction, and a purified sample of high purity was able to be obtained.

pG-D153H/D330N

Figure 12:
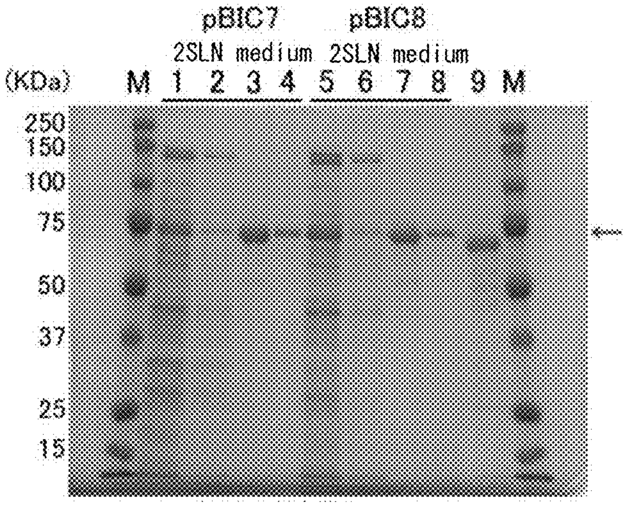
FIG. 12 is a diagram illustrating the purification of an expressed protein (pG-D153H/D330N) using a Ni-NTA column in Example 2 (vectors: pBIC7, pBIC8, medium: 2SLN, the arrow indicates the electrophoretic position of pG-D153H/D330N).
Figure 13:
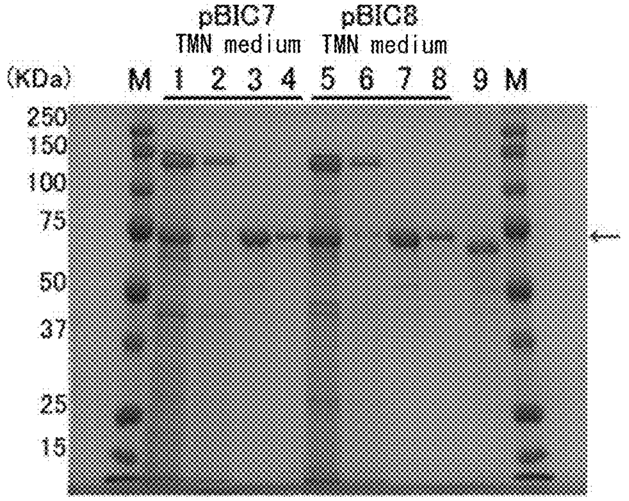
FIG. 13 is a diagram illustrating the purification of an expressed protein (pG-D153H/D330N) using a Ni-NTA column in Example 2 (vectors: pBIC7, pBIC8, medium: TMN, the arrow indicates the electrophoretic position of pG-D153H/D330N).

In the case of pG-D153H/D330N, samples of high purity were able to be purified for combinations with pBIC7 and pBIC8 in both the 2SLN medium and the TMN medium. Further, measurement of the molecular weights of the purified samples yielded similar results to pG-D153G/D330N (FIGS. 12 and 13).

pG-K328R/D330N (pG-binding site: N-terminal)

In the case where the 2SLN medium was used, purification using the Ni-NTA column was possible for pBIC4, and a purified sample of high purity was able to be obtained. However, for pBIC8, only a small amount of protein existed in the column unbound fraction, and a similar result was also observed in subsequent column washing. The fact that almost no protein was collected even when an elution buffer having a high imidazole concentration was used indicated a possibility that the protein may have bound strongly to the Ni-NTA column and could not be recovered (FIG. 14). In the case of the TMN medium, the target protein was able to be purified for both pBIC4 and pBIC8 (FIG. 15). The reason that pBIC8 adsorbed to the column only when the 2SLN medium was used remains unclear.

pG-K328R/D330N (pG-binding site: C-terminal)

In the case of pG-K328R/D330N (pG-binding site: C-terminal), simple purification was performed in a similar manner for those combinations for which a high protein expression level was confirmed (FIGS. 16 and 17). Purified samples were able to be obtained for pBIC1, pBIC2 and pBIC 3 in the 2SLN medium, and for pBIC1 and pBIC3 in the TMN medium.

Example 3

In order to ascertain whether the enzyme portion of each purified sample and the antibody-bound protein portion actually functioned, and determine whether or not the portions could be used as protein detection reagents, an alkaline phosphatase (ALP) activity measurement and a detection sensitivity measurement by Western blot analysis were conducted using a commercially available reagent as a control.

Materials and Experimental Method

1. ALP Activity Measurement

The purified sample was diluted to a prescribed concentration using an enzyme dilution buffer, and 5 μL of the dilute solution was added to each well of a 96-well microplate. Subsequently, 95 μL of a substrate (p-NPP: p-nitrophenyl phosphate, 149-02342/Wako Pure Chemical Industries) solution was added, and the change in absorbance (OD410) generated as a result of dephosphorylation of the substrate was measured 18 times, every 20 to 30 seconds, using a microplate reader (SH-9000 Lab/Corona Electric). The measurement temperature was 45° C. The specific activity (μmol p-NP/mg protein/sec) of the enzyme was determined using a calibration curve prepared using known concentrations of the enzyme product (p-NP: p-nitrophenol, 299-58641/Wako Pure Chemical Industries). The buffers described below were used for dilution of the enzyme, and dissolution and dilution of the substrate and the enzyme product, and the p-NPP concentration of the substrate solution was set to 1 mM. CIAP (which is calf intestine-derived ALP) that had been expressed in yeast (AP highly active rec. EIA Grade, CR, 03 535 452/Roche) and PLAP (Placental Alkaline Phosphatase, P3895/Sigma) were used for the purposes of comparison.

Enzyme dilution buffer: 100 mM DEA-HCl (pH 9.5), 1 mM $MgCl_2$

Substrate, enzyme product dilution and dissolution buffer: 1 M DEA-HCl (pH 9.5), 1 mM $MgCl_2$ 2. Detection Sensitivity Investigation by Western Blot Human-derived Transferrin (Calbiochem/616419), which is a blood serum protein, was used for the antigen. Dilute samples were prepared by dilution with a 2× sample buffer to obtain concentrations of 10 ng to 3 pg/15 μL, 15 μL of each sample was loaded per lane, and SDS-PAGE was performed. Hybond P (PVDF) membranes to which Transferrin of the same dilution samples had been transferred were also prepared, and following antigen-antibody reaction, the detection sensitivity was compared. A more detailed description of the procedure and the reagents used for comparative purposes is presented below.

Sample buffer (2×): 62.5 mM Tris-HCl (pH 6.8), 2% SDS, 25% glycerol, 0.01% BPB (Bromophenol blue, 029-02912/Wako), 10% mercaptoethanol (M3148/Sigma)

1) SDS-PAGE (200 V constant voltage conditions, 30 min)

Gel: Mini PROTEAN TGX gel 10% (Bio-Rad/456-1035)

Electrophoresis buffer: 25 mM Tris-HCl (pH 8.3), 192 mM glycerol, 0.1% SDS

2) Blotting (200 mA constant current conditions, 40 min)

Membrane: Hybond P membrane (GE Healthcare/RPN2020F)

Transfer buffer: 25 mM Tris-HCl (pH 8.3), 192 mM glycerol, 20% methanol

3) Membrane washing (TBS, 3 min×2 repetitions)

TBS (20 mM Tris-HCl (pH 7.5), 150 mM NaCl, 2.68 mM KCl)

4) Blocking (5% Skim Milk Powder (198-10605/Wako)/TBST, room temperature, stirring, 60 min)

TBST (0.1% Tween20/TBS)

5) Membrane washing (TBST, 5 min×3 repetitions)

6) Primary antibody reaction (room temperature, stirring, 60 min)

Antibody: Rabbit anti-human Transferrin antibody (DAKO/A0061) 1/2,000 dilution (4.3 μg/mL TBST)

7) Membrane washing (TBST, 5 min×4 repetitions)

8) pG-alkaline phosphatase reaction (room temperature, stirring, 60 min)

pG-BAP mutant purified sample, Fr. 1 used

Treatment concentration: 0.5 μg/mL TBST

9) Membrane washing (TBST, 5 min×4 repetitions)

10) Luminescence detection

Image acquired every 150 sec until 7,200 sec

Measurement device: ChemiDoc XRS+ (170-8265J1PC/Bio-Rad)

Luminescent substrate: CDP-Star Ready-to-use (Roche/12041677001)

Comparative reagent: pG-CIAP (Protein G Alkaline Phosphatase Conjugated, PG00-05/Rockland)

Results

1. ALP Activity

FIG. 18 illustrates the results of measuring the ALP activity of pG-D153G/D330N and pG-D153H/D330N (both having pG binding site: N-terminal). Although the variations in the measured value were quite large, the specific activity of pG-D153G/D330N was from 350 to 450 μmol p-NP/mg prot./min, and the specific activity tended to be slightly higher in the TMN medium.

On the other hand, the specific activity of pG-D153H/D330N was about 50 μmol p-NP/mg prot./min, indicating a significantly lower activity compared with pG-D153G/D330N.

FIG. 19 illustrates the results of measuring the activity of pG-K328R/D330N (pG binding site: N-terminal or C-terminal). The N-terminal bound structure exhibited a slightly greater variation in the activity value, but both the N-terminal and the C-terminal structures had a specific activity of about 200 μmol p-NP/mg prot./min, and it is considered that there was little difference between the two.

Based on the above results, listing the prepared pG-BAP mutants in terms of decreasing ALP activity yielded the following:

pG-D153G/D330N>pG-K328R/D330N>pG-D153H/D330N

2. Detection Sensitivity by Western Blot

The results of performing a Western blot analysis using the purified samples (Fr. 1), and then detecting the light emission are shown in FIGS. 20 to 23. In the case of pG-D153G/D330N, with the exception of pBIC8 (2SLN medium), 3 to 10 pg of Transferrin was able to be detected. The fact that the detection sensitivity of the control pG-CIAP was about 100 pg indicated that the detection sensitivity of pG-D153G/D330N was potentially 10 to 30 times higher (FIG. 20). In contrast, the detection sensitivity of pG-D153H/D330N was 30 to 100 pg, which was little different from the commercially available pG-CIAP, and it is thought that this low detection sensitivity is a reflection of the low enzyme activity (FIG. 21). In the case of pG-K328R/D330N, the detection sensitivity was slightly inferior to that of pG-D153G/D330N, but both the structure in which pG was bound at the N-terminal and the structure in which pG was bound at the C-terminal exhibited detection sensitivity of about 10 pg, indicating that the detection sensitivity was potentially about 10 times higher than that of the control pG-CIAP (FIGS. 22 and 23).

Based on the above results, it was clear that the target protein that had produced by secretory expression in *Brevibacillus* had retained its antibody-binding activity and ALP activity. Further, in Western blot analysis, which represents an actual application, the tested pG-D153G/D330N and pG-K328R/D330N exhibited higher detection sensitivity than a known commercially available product, confirming their usefulness as protein detection reagents.

In the case of pG-K328R/D330N, there was almost no difference in performance between the N-terminal structure and the C-terminal structure in terms of ALP activity and Western blot results.

In the cases of D153G/D330N and D153H/D330N, only the N-terminal was investigated as the pG binding site, but these mutation sites are close to phosphate, $Mg^{2+}$ and $Zn^{2+}$ binding sites, and it is thought that even if the pG binding site was shifted to the C-terminal, it would be unlikely for the change in three-dimensional structure to impair the pG antibody-binding activity, meaning there is a high probability that similar performance results could be obtained.

In the case of K328R/D330N, the stability of production by expression was superior for the N-terminal structure. It is thought that one reason for this observation may be that in the case of the structure in which pG is bound to the C-terminal, it may be difficult to retain the vector in a stable manner inside the host.

The invention claimed is:

1. A fusion protein for protein detection, the fusion protein comprising:

three IgG-binding domains which are the B domain of protein A, the C2 domain of protein G and the C3 domain of protein G that are linked, wherein the three IgG-binding domains are fused via the B domain of protein A to a C-terminal side or an N-terminal side of a double mutant of *Escherichia coli* alkaline phosphatase (BAP), wherein the double mutant of BAP is at least one of a double mutant D153G/D330N of BAP in which an amino acid residue Asp at position 153 has been substituted by Gly and an amino acid residue Asp at position 330 has been substituted by Asn, a double mutant D153H/D330N of BAP in which an amino acid residue Asp at position 153 has been substituted by His and an amino acid residue Asp at position 330 has been substituted by Asn, or a double mutant K328R/D330N of BAP in which an amino acid residue Lys at position 328 has been substituted by Arg and an amino acid residue Asp at position 330 has been substituted by Asn; and wherein the fusion protein includes:

an amino acid sequence as set forth in SEQ ID NO: 1 when the double mutant of BAP is the double mutant D153G/D330N of BAP, an amino acid sequence as set forth in SEQ ID NO: 3 when the double mutant of BAP is the double mutant D153H/D330N of BAP, and an amino acid sequence as set forth in SEQ ID NO: 5 or SEQ ID NO: 7 when the double mutant of BAP is the double mutant K328R/D330N of BAP.

2. A method for detecting a protein, the method comprising:

binding, either directly or indirectly, the fusion protein for protein detection according to claim 1 and the protein that exists within a target material, wherein the protein to be detected includes the IgG, and detecting an alkaline phosphatase portion of the bound fusion protein for protein detection as a labeling portion.

* * * * *

SEQUENCE LISTING

```
<160> NUMBER OF SEQ ID NOS: 14

<210> SEQ ID NO 1
<211> LENGTH: 666
<212> TYPE: PRT
<213> ORGANISM: Artificial Sequence
<220> FEATURE:
<223> OTHER INFORMATION: Synthesized

<400> SEQUENCE: 1

Ala Asp Thr Tyr Lys Leu Val Ile Asn Gly Lys Thr Leu Lys Gly Glu
1               5                   10                  15

Thr Thr Thr Glu Ala Val Asp Ala Ala Thr Ala Glu Lys Val Phe Lys
            20                  25                  30

Gln Tyr Ala Asn Asp Asn Gly Val Asp Gly Glu Trp Thr Tyr Asp Asp
        35                  40                  45

Ala Thr Lys Thr Phe Thr Val Thr Glu Lys Pro Glu Val Ile Asp Ala
    50                  55                  60

Ser Glu Leu Thr Pro Ala Val Thr Thr Tyr Lys Leu Val Ile Asn Gly
65                  70                  75                  80

Lys Thr Leu Lys Gly Glu Thr Thr Thr Lys Ala Val Asp Ala Glu Thr
                85                  90                  95

Ala Glu Lys Ala Phe Lys Gln Tyr Ala Asn Asp Asn Gly Val Asp Gly
            100                 105                 110

Val Trp Thr Tyr Asp Asp Ala Thr Lys Thr Phe Thr Val Thr Glu Gly
        115                 120                 125

Gly Gly Gly Ser Asp Val Asp Asn Lys Phe Asn Lys Glu Gln Gln Asn
    130                 135                 140

Ala Phe Trp Glu Ile Leu His Leu Pro Asn Leu Asn Glu Glu Gln Arg
145                 150                 155                 160

Asn Gly Phe Ile Gln Ser Leu Lys Asp Asp Pro Ser Gln Ser Ala Asn
                165                 170                 175

Leu Leu Ala Glu Ala Lys Lys Leu Asn Asp Ala Gln Ala Pro Lys Gly
            180                 185                 190

Gly Gly Gly Ser Thr Pro Glu Met Pro Val Leu Glu Asn Arg Ala Ala
        195                 200                 205

Gln Gly Asp Ile Thr Ala Pro Gly Gly Ala Arg Arg Leu Thr Gly Asp
    210                 215                 220
```

-continued

```
Gln Thr Ala Ala Leu Arg Asp Ser Leu Ser Asp Lys Pro Ala Lys Asn
225                 230                 235                 240

Ile Ile Leu Leu Ile Gly Asp Gly Met Gly Asp Ser Glu Ile Thr Ala
                245                 250                 255

Ala Arg Asn Tyr Ala Glu Gly Ala Gly Gly Phe Phe Lys Gly Ile Asp
            260                 265                 270

Ala Leu Pro Leu Thr Gly Gln Tyr Thr His Tyr Ala Leu Asn Lys Lys
        275                 280                 285

Thr Gly Lys Pro Asp Tyr Val Thr Asp Ser Ala Ala Ser Ala Thr Ala
    290                 295                 300

Trp Ser Thr Gly Val Lys Thr Tyr Asn Gly Ala Leu Gly Val Asp Ile
305                 310                 315                 320

His Glu Lys Asp His Pro Thr Ile Leu Glu Met Ala Lys Ala Ala Gly
                325                 330                 335

Leu Ala Thr Gly Asn Val Ser Thr Ala Gln Leu Gln Gly Ala Thr Pro
            340                 345                 350

Ala Ala Leu Val Ala His Val Thr Ser Arg Lys Cys Tyr Gly Pro Ser
        355                 360                 365

Ala Thr Ser Glu Lys Cys Pro Gly Asn Ala Leu Glu Lys Gly Gly Lys
    370                 375                 380

Gly Ser Ile Thr Glu Gln Leu Leu Asn Ala Arg Ala Asp Val Thr Leu
385                 390                 395                 400

Gly Gly Gly Ala Lys Thr Phe Ala Glu Thr Ala Thr Ala Gly Glu Thr
                405                 410                 415

Gln Gly Lys Thr Leu Arg Glu Gln Ala Gln Ala Arg Gly Tyr Gln Leu
            420                 425                 430

Val Ser Asp Ala Ala Ser Leu Asn Ser Val Thr Glu Ala Asn Gln Gln
        435                 440                 445

Lys Pro Leu Leu Gly Leu Phe Ala Asp Gly Asn Met Pro Val Arg Trp
    450                 455                 460

Leu Gly Pro Lys Ala Thr Tyr His Gly Asn Ile Asp Lys Pro Ala Val
465                 470                 475                 480

Thr Cys Thr Pro Asn Pro Gln Arg Asn Asp Ser Val Pro Thr Leu Ala
                485                 490                 495

Gln Met Thr Asp Lys Ala Ile Glu Leu Leu Ser Lys Asn Glu Lys Gly
            500                 505                 510

Phe Phe Leu Gln Val Glu Gly Ala Ser Ile Asp Lys Gln Asn His Ala
        515                 520                 525

Ala Asn Pro Cys Gly Gln Ile Gly Glu Thr Val Asp Leu Asp Glu Ala
    530                 535                 540

Val Gln Arg Ala Leu Glu Phe Ala Lys Lys Glu Gly Asn Thr Leu Val
545                 550                 555                 560

Ile Val Thr Ala Asp His Ala His Ala Ser Gln Ile Val Ala Pro Asp
                565                 570                 575

Thr Lys Ala Pro Gly Leu Thr Gln Ala Leu Asn Thr Lys Asp Gly Ala
            580                 585                 590

Val Met Val Met Ser Tyr Gly Asn Ser Glu Glu Asp Ser Gln Glu His
        595                 600                 605

Thr Gly Ser Gln Leu Arg Ile Ala Ala Tyr Gly Pro His Ala Ala Asn
    610                 615                 620

Val Val Gly Leu Thr Asp Gln Thr Asp Leu Phe Tyr Thr Met Lys Ala
625                 630                 635                 640
```

-continued

```
Ala Leu Gly Leu Lys Leu Glu Gly Ser His His His His His His Gly
                645                 650                 655

Gly Gly Gly Ser Met Arg His Lys Gly Ser
            660                 665


<210> SEQ ID NO 2
<211> LENGTH: 1998
<212> TYPE: DNA
<213> ORGANISM: Artificial Sequence
<220> FEATURE:
<223> OTHER INFORMATION: Synthesized

<400> SEQUENCE: 2

gcagatacgt ataaactcgt catcaacggt aaaacgttaa aaggcgaaac taccactgaa      60

gctgttgatg ctgctacggc agaaaaagtg ttcaaacagt acgcgaatga caatggcgtg     120

gatggcgagt ggacttacga tgacgcgact aaaactttca ccgttaccga aaagccggaa     180

gtaattgacg cttccgaact gaccccggca gtcacgactt acaaattggt cattaacggg     240

aaaaccctta aaggggaaac caccactaag gcggttgacg cggaaacggc cgagaaagcg     300

ttcaagcagt atgctaacga caatggtgtt gatggcgtgt ggacctatga tgatgctaca     360

aaaacattta cggtgaccga aggtggcggc ggttccgatg tcgacaataa gttcaataaa     420

gagcagcaga acgccttctg ggagattctc cacctcccga atctgaacga ggagcagcgt     480

aacggtttta ttcaatctct gaaagacgat ccgtcacaga gcgctaacct gctggcagaa     540

gcaaaaaaat taaatgatgc ccaggcgccg aaaggcggtg gggatccaac gcccgaaatg     600

cccgtgttgg agaaccgcgc tgcacagggt gatatcacgg ccccaggcgg tgcccgtcgc     660

ctcacgggag accaaaccgc agccttgcgt gacagccttt ccgataaacc tgcaaaaaac     720

attatcttgc ttattggcga cggtatgggc gattccgaaa ttacggccgc gcgcaattat     780

gccgaaggcg ctggtggctt cttcaagggg attgatgcgt taccactgac agggcagtac     840

actcactacg cgctcaacaa aaaaaccggt aagccagatt acgtaaccga ctctgctgcg     900

agcgccacag cctggtcaac tggtgtgaaa acttataacg gcgccttagg cgtcgacatt     960

cacgaaaaag atcacccgac gattctggaa atggcgaaag cggccggtct ggcgacggga    1020

aacgtgtcta cggcggaact ccagggcgcg acgcccgccg cactggtggc ccatgtgacc    1080

tctcgtaagt gctacggccc tagtgcgacc tcggagaaat gcccaggcaa tgctctggaa    1140

aaagggggca agggttctat tactgagcag ctgctgaatg cgcgcgctga tgtgacgctg    1200

ggtggcggag caaaaacctt tgccgaaacc gccactgccg gtgagtggca ggggaaaact    1260

ctgcgcgaac aggcgcaagc ccgcggatat caactggtgt ctgatgcggc gtcgctgaac    1320

tccgtaaccg aagcgaacca gcagaaaccg cttctgggtc tgttcgcaga tggcaatatg    1380

cctgtgcgtt ggctggggcc caaagcaacg tatcacggca acatcgataa gcctgctgta    1440

acgtgtacgc cgaacccgca gcgtaatgat agtgtaccga cactcgcgca gatgaccgat    1500

aaagcaatcg agctgctgtc gaagaacgaa aaaggttttt tcctgcaagt tgagggcgcg    1560

agcattgata aacagaacca tgccgctaac ccctgcggcc agatcgggga aacggttgat    1620

ctggatgagg ctgtacagcg tgctctggaa tttgcgaaaa aagagggtaa taccttagtg    1680

attgttaccg cagaccacgc acacgctagc cagatcgttg caccggacac taaggcaccg    1740

ggcctgaccc aggctctgaa caccaaggac ggggcggtta tggttatgtc ctatggtaac    1800

tcggaagagg actcccaaga acataccggt tcgcaattac gcatcgcggc gtatggtccg    1860

catgcagcga acgtagtggg tctgaccgat cagaccgatc tgttctatac aatgaaagcc    1920
```

gcgttgggac tcaaactgga gggatcccat catcatcacc atcacggtgg cggtggtagc 1980
atgcgccata aaggctcg 1998

<210> SEQ ID NO 3
<211> LENGTH: 666
<212> TYPE: PRT
<213> ORGANISM: Artificial Sequence
<220> FEATURE:
<223> OTHER INFORMATION: Synthesized

<400> SEQUENCE: 3

Ala Asp Thr Tyr Lys Leu Val Ile Asn Gly Lys Thr Leu Lys Gly Glu
1 5 10 15

Thr Thr Thr Glu Ala Val Asp Ala Ala Thr Ala Glu Lys Val Phe Lys
20 25 30

Gln Tyr Ala Asn Asp Asn Gly Val Asp Gly Glu Trp Thr Tyr Asp Asp
35 40 45

Ala Thr Lys Thr Phe Thr Val Thr Glu Lys Pro Glu Val Ile Asp Ala
50 55 60

Ser Glu Leu Thr Pro Ala Val Thr Thr Tyr Lys Leu Val Ile Asn Gly
65 70 75 80

Lys Thr Leu Lys Gly Glu Thr Thr Thr Lys Ala Val Asp Ala Glu Thr
85 90 95

Ala Glu Lys Ala Phe Lys Gln Tyr Ala Asn Asp Asn Gly Val Asp Gly
100 105 110

Val Trp Thr Tyr Asp Asp Ala Thr Lys Thr Phe Thr Val Thr Glu Gly
115 120 125

Gly Gly Gly Ser Asp Val Asp Asn Lys Phe Asn Lys Glu Gln Gln Asn
130 135 140

Ala Phe Trp Glu Ile Leu His Leu Pro Asn Leu Asn Glu Glu Gln Arg
145 150 155 160

Asn Gly Phe Ile Gln Ser Leu Lys Asp Asp Pro Ser Gln Ser Ala Asn
165 170 175

Leu Leu Ala Glu Ala Lys Lys Leu Asn Asp Ala Gln Ala Pro Lys Gly
180 185 190

Gly Gly Gly Ser Thr Pro Glu Met Pro Val Leu Glu Asn Arg Ala Ala
195 200 205

Gln Gly Asp Ile Thr Ala Pro Gly Gly Ala Arg Arg Leu Thr Gly Asp
210 215 220

Gln Thr Ala Ala Leu Arg Asp Ser Leu Ser Asp Lys Pro Ala Lys Asn
225 230 235 240

Ile Ile Leu Leu Ile Gly Asp Gly Met Gly Asp Ser Glu Ile Thr Ala
245 250 255

Ala Arg Asn Tyr Ala Glu Gly Ala Gly Gly Phe Phe Lys Gly Ile Asp
260 265 270

Ala Leu Pro Leu Thr Gly Gln Tyr Thr His Tyr Ala Leu Asn Lys Lys
275 280 285

Thr Gly Lys Pro Asp Tyr Val Thr Asp Ser Ala Ala Ser Ala Thr Ala
290 295 300

Trp Ser Thr Gly Val Lys Thr Tyr Asn Gly Ala Leu Gly Val Asp Ile
305 310 315 320

His Glu Lys Asp His Pro Thr Ile Leu Glu Met Ala Lys Ala Ala Gly
325 330 335

Leu Ala Thr Gly Asn Val Ser Thr Ala Gln Leu Gln His Ala Thr Pro

-continued

```
            340                 345                 350

Ala Ala Leu Val Ala His Val Thr Ser Arg Lys Cys Tyr Gly Pro Ser
        355                 360                 365

Ala Thr Ser Glu Lys Cys Pro Gly Asn Ala Leu Glu Lys Gly Gly Lys
    370                 375                 380

Gly Ser Ile Thr Glu Gln Leu Leu Asn Ala Arg Ala Asp Val Thr Leu
385                 390                 395                 400

Gly Gly Gly Ala Lys Thr Phe Ala Glu Thr Ala Thr Ala Gly Glu Thr
                405                 410                 415

Gln Gly Lys Thr Leu Arg Glu Gln Ala Gln Ala Arg Gly Tyr Gln Leu
            420                 425                 430

Val Ser Asp Ala Ala Ser Leu Asn Ser Val Thr Glu Ala Asn Gln Gln
        435                 440                 445

Lys Pro Leu Leu Gly Leu Phe Ala Asp Gly Asn Met Pro Val Arg Trp
    450                 455                 460

Leu Gly Pro Lys Ala Thr Tyr His Gly Asn Ile Asp Lys Pro Ala Val
465                 470                 475                 480

Thr Cys Thr Pro Asn Pro Gln Arg Asn Asp Ser Val Pro Thr Leu Ala
                485                 490                 495

Gln Met Thr Asp Lys Ala Ile Glu Leu Leu Ser Lys Asn Glu Lys Gly
            500                 505                 510

Phe Phe Leu Gln Val Glu Gly Ala Ser Ile Asp Lys Gln Asn His Ala
        515                 520                 525

Ala Asn Pro Cys Gly Gln Ile Gly Glu Thr Val Asp Leu Asp Glu Ala
    530                 535                 540

Val Gln Arg Ala Leu Glu Phe Ala Lys Lys Glu Gly Asn Thr Leu Val
545                 550                 555                 560

Ile Val Thr Ala Asp His Ala His Ala Ser Gln Ile Val Ala Pro Asp
                565                 570                 575

Thr Lys Ala Pro Gly Leu Thr Gln Ala Leu Asn Thr Lys Asp Gly Ala
            580                 585                 590

Val Met Val Met Ser Tyr Gly Asn Ser Glu Glu Asp Ser Gln Glu His
        595                 600                 605

Thr Gly Ser Gln Leu Arg Ile Ala Ala Tyr Gly Pro His Ala Ala Asn
    610                 615                 620

Val Val Gly Leu Thr Asp Gln Thr Asp Leu Phe Tyr Thr Met Lys Ala
625                 630                 635                 640

Ala Leu Gly Leu Lys Leu Glu Gly Ser His His His His His His Gly
                645                 650                 655

Gly Gly Gly Ser Met Arg His Lys Gly Ser
            660                 665


<210> SEQ ID NO 4
<211> LENGTH: 1998
<212> TYPE: DNA
<213> ORGANISM: Artificial Sequence
<220> FEATURE:
<223> OTHER INFORMATION: Synthesized

<400> SEQUENCE: 4

gcagatacgt ataaactcgt catcaacggt aaaacgttaa aaggcgaaac taccactgaa      60

gctgttgatg ctgctacggc agaaaaagtg ttcaaacagt acgcgaatga caatggcgtg     120

gatggcgagt ggacttacga tgacgcgact aaaactttca ccgttaccga aaagccggaa     180

gtaattgacg cttccgaact gaccccggca gtcacgactt acaaattggt cattaacggg     240
```

```
aaaaccctta aaggggaaac caccactaag gcggttgacg cggaaacggc cgagaaagcg    300
ttcaagcagt atgctaacga caatggtgtt gatggcgtgt ggacctatga tgatgctaca    360
aaaacattta cggtgaccga aggtggcggc ggttccgatg tcgacaataa gttcaataaa    420
gagcagcaga acgccttctg ggagattctc cacctcccga atctgaacga ggagcagcgt    480
aacggtttta ttcaatctct gaaagacgat ccgtcacaga gcgctaacct gctggcagaa    540
gcaaaaaaat taaatgatgc ccaggcgccg aaaggcggtg ggggatccac gcccgaaatg    600
cccgtgttgg agaaccgcgc tgcacagggt gatatcacgg ccccaggcgg tgcccgtcgc    660
ctcacgggag accaaaccgc agccttgcgt gacagccttt ccgataaacc tgcaaaaaac    720
attatcttgc ttattggcga cggtatgggc gattccgaaa ttacggccgc gcgcaattat    780
gccgaaggcg ctggtggctt cttcaagggg attgatgcgt taccactgac agggcagtac    840
actcactacg cgctcaacaa aaaaaccggt aagccagatt acgtaaccga ctctgctgcg    900
agcgccacag cctggtcaac tggtgtgaaa acttataacg gcgccttagg cgtcgacatt    960
cacgaaaaag atcacccgac gattctggaa atggcgaaag cggccggtct ggcgacggga   1020
aacgtgtcta cggcggaact ccagcatgcg acgcccgccg cactggtggc ccatgtgacc   1080
tctcgtaagt gctacggccc tagtgcgacc tcggagaaat gcccaggcaa tgctctggaa   1140
aaagggggca agggttctat tactgagcag ctgctgaatg cgcgcgctga tgtgacgctg   1200
ggtggcggag caaaaacctt tgccgaaacc gccactgccg gtgagtggca ggggaaaact   1260
ctgcgcgaac aggcgcaagc ccgcggatat caactggtgt ctgatgcggc gtcgctgaac   1320
tccgtaaccg aagcgaacca gcagaaaccg cttctgggtc tgttcgcaga tggcaatatg   1380
cctgtgcgtt ggctggggcc caaagcaacg tatcacggca acatcgataa gcctgctgta   1440
acgtgtacgc cgaacccgca gcgtaatgat agtgtaccga cactcgcgca gatgaccgat   1500
aaagcaatcg agctgctgtc gaagaacgaa aaaggttttt tcctgcaagt tgagggcgcg   1560
agcattgata aacagaacca tgccgctaac ccctgcggcc agatcgggga aacggttgat   1620
ctggatgagg ctgtacagcg tgctctggaa tttgcgaaaa aagagggtaa taccttagtg   1680
attgttaccg cagaccacgc acacgctagc cagatcgttg caccggacac taaggcaccg   1740
ggcctgaccc aggctctgaa caccaaggac ggggcggtta tggttatgtc ctatggtaac   1800
tcggaagagg actcccaaga acataccggt tcgcaattac gcatcgcggc gtatggtccg   1860
catgcagcga acgtagtggg tctgaccgat cagaccgatc tgttctatac aatgaaagcc   1920
gcgttgggac tcaaactgga gggatcccat catcatcacc atcacggtgg cggtggtagc   1980
atgcgccata aaggctcg                                                 1998
```

<210> SEQ ID NO 5
<211> LENGTH: 666
<212> TYPE: PRT
<213> ORGANISM: Artificial Sequence
<220> FEATURE:
<223> OTHER INFORMATION: Synthesized

<400> SEQUENCE: 5

```
Ala Asp Thr Tyr Lys Leu Val Ile Asn Gly Lys Thr Leu Lys Gly Glu
1               5                   10                  15

Thr Thr Thr Glu Ala Val Asp Ala Ala Thr Ala Glu Lys Val Phe Lys
            20                  25                  30

Gln Tyr Ala Asn Asp Asn Gly Val Asp Gly Glu Trp Thr Tyr Asp Asp
        35                  40                  45
```

-continued

```
Ala Thr Lys Thr Phe Thr Val Thr Glu Lys Pro Glu Val Ile Asp Ala
    50                  55                  60

Ser Glu Leu Thr Pro Ala Val Thr Thr Tyr Lys Leu Val Ile Asn Gly
65                  70                  75                  80

Lys Thr Leu Lys Gly Glu Thr Thr Thr Lys Ala Val Asp Ala Glu Thr
                85                  90                  95

Ala Glu Lys Ala Phe Lys Gln Tyr Ala Asn Asp Asn Gly Val Asp Gly
            100                 105                 110

Val Trp Thr Tyr Asp Asp Ala Thr Lys Thr Phe Thr Val Thr Glu Gly
        115                 120                 125

Gly Gly Gly Ser Asp Val Asp Asn Lys Phe Asn Lys Glu Gln Gln Asn
    130                 135                 140

Ala Phe Trp Glu Ile Leu His Leu Pro Asn Leu Asn Glu Glu Gln Arg
145                 150                 155                 160

Asn Gly Phe Ile Gln Ser Leu Lys Asp Asp Pro Ser Gln Ser Ala Asn
                165                 170                 175

Leu Leu Ala Glu Ala Lys Lys Leu Asn Asp Ala Gln Ala Pro Lys Gly
            180                 185                 190

Gly Gly Gly Ser Thr Pro Glu Met Pro Val Leu Glu Asn Arg Ala Ala
        195                 200                 205

Gln Gly Asp Ile Thr Ala Pro Gly Gly Ala Arg Arg Leu Thr Gly Asp
    210                 215                 220

Gln Thr Ala Ala Leu Arg Asp Ser Leu Ser Asp Lys Pro Ala Lys Asn
225                 230                 235                 240

Ile Ile Leu Leu Ile Gly Asp Gly Met Gly Asp Ser Glu Ile Thr Ala
                245                 250                 255

Ala Arg Asn Tyr Ala Glu Gly Ala Gly Gly Phe Phe Lys Gly Ile Asp
            260                 265                 270

Ala Leu Pro Leu Thr Gly Gln Tyr Thr His Tyr Ala Leu Asn Lys Lys
        275                 280                 285

Thr Gly Lys Pro Asp Tyr Val Thr Asp Ser Ala Ala Ser Ala Thr Ala
    290                 295                 300

Trp Ser Thr Gly Val Lys Thr Tyr Asn Gly Ala Leu Gly Val Asp Ile
305                 310                 315                 320

His Glu Lys Asp His Pro Thr Ile Leu Glu Met Ala Lys Ala Ala Gly
                325                 330                 335

Leu Ala Thr Gly Asn Val Ser Thr Ala Gln Leu Gln Gly Ala Thr Pro
            340                 345                 350

Ala Ala Leu Val Ala His Val Thr Ser Arg Lys Cys Tyr Gly Pro Ser
        355                 360                 365

Ala Thr Ser Glu Lys Cys Pro Gly Asn Ala Leu Glu Lys Gly Gly Lys
    370                 375                 380

Gly Ser Ile Thr Glu Gln Leu Leu Asn Ala Arg Ala Asp Val Thr Leu
385                 390                 395                 400

Gly Gly Gly Ala Lys Thr Phe Ala Glu Thr Ala Thr Ala Gly Glu Thr
                405                 410                 415

Gln Gly Lys Thr Leu Arg Glu Gln Ala Gln Ala Arg Gly Tyr Gln Leu
            420                 425                 430

Val Ser Asp Ala Ala Ser Leu Asn Ser Val Thr Glu Ala Asn Gln Gln
        435                 440                 445

Lys Pro Leu Leu Gly Leu Phe Ala Asp Gly Asn Met Pro Val Arg Trp
    450                 455                 460
```

-continued

Leu Gly Pro Lys Ala Thr Tyr His Gly Asn Ile Asp Lys Pro Ala Val
465 470 475 480

Thr Cys Thr Pro Asn Pro Gln Arg Asn Asp Ser Val Pro Thr Leu Ala
485 490 495

Gln Met Thr Asp Lys Ala Ile Glu Leu Leu Ser Lys Asn Glu Lys Gly
500 505 510

Phe Phe Leu Gln Val Glu Gly Ala Ser Ile Asp Arg Gln Asn His Ala
515 520 525

Ala Asn Pro Cys Gly Gln Ile Gly Glu Thr Val Asp Leu Asp Glu Ala
530 535 540

Val Gln Arg Ala Leu Glu Phe Ala Lys Lys Glu Gly Asn Thr Leu Val
545 550 555 560

Ile Val Thr Ala Asp His Ala His Ala Ser Gln Ile Val Ala Pro Asp
565 570 575

Thr Lys Ala Pro Gly Leu Thr Gln Ala Leu Asn Thr Lys Asp Gly Ala
580 585 590

Val Met Val Met Ser Tyr Gly Asn Ser Glu Glu Asp Ser Gln Glu His
595 600 605

Thr Gly Ser Gln Leu Arg Ile Ala Ala Tyr Gly Pro His Ala Ala Asn
610 615 620

Val Val Gly Leu Thr Asp Gln Thr Asp Leu Phe Tyr Thr Met Lys Ala
625 630 635 640

Ala Leu Gly Leu Lys Leu Glu Gly Ser His His His His His His Gly
645 650 655

Gly Gly Gly Ser Met Arg His Lys Gly Ser
660 665

<210> SEQ ID NO 6
<211> LENGTH: 1998
<212> TYPE: DNA
<213> ORGANISM: Artificial Sequence
<220> FEATURE:
<223> OTHER INFORMATION: Synthesized

<400> SEQUENCE: 6
gcagatacgt ataaactcgt catcaacggt aaaacgttaa aaggcgaaac taccactgaa 60
gctgttgatg ctgctacggc agaaaaagtg ttcaaacagt acgcgaatga caatggcgtg 120
gatggcgagt ggacttacga tgacgcgact aaaactttca ccgttaccga aaagccggaa 180
gtaattgacg cttccgaact gaccccggca gtcacgactt acaaattggt cattaacggg 240
aaaaccctta aaggggaaac caccactaag gcggttgacg cggaaacggc cgagaaagcg 300
ttcaagcagt atgctaacga caatggtgtt gatggcgtgt ggacctatga tgatgctaca 360
aaaacattta cggtgaccga aggtggcggc ggttccgatg tcgacaataa gttcaataaa 420
gagcagcaga acgccttctg ggagattctc cacctcccga atctgaacga ggagcagcgt 480
aacggtttta ttcaatctct gaaagacgat ccgtcacaga gcgctaacct gctggcagaa 540
gcaaaaaaat taaatgatgc ccaggcgccg aaaggcggtg ggggatccac gcccgaaatg 600
cccgtgttgg agaaccgcgc tgcacagggt gatatcacgg ccccaggcgg tgcccgtcgc 660
ctcacgggag accaaaccgc agccttgcgt gacagccttt ccgataaacc tgcaaaaaac 720
attatcttgc ttattggcga cggtatgggc gattccgaaa ttacggccgc gcgcaattat 780
gccgaaggcg ctggtggctt cttcaagggg attgatgcgt taccactgac agggcagtac 840
actcactacg cgctcaacaa aaaaaccggt aagccagatt acgtaaccga ctctgctgcg 900

-continued agcgccacag cctggtcaac tggtgtgaaa acttataacg gcgccttagg cgtcgacatt 960
cacgaaaaag atcacccgac gattctggaa atggcgaaag cggccggtct ggcgacggga 1020
aacgtgtcta cggcggaact ccaggacgcg acgcccgccg cactggtggc ccatgtgacc 1080
tctcgtaagt gctacggccc tagtgcgacc tcggagaaat gcccaggcaa tgctctggaa 1140
aaagggggca agggttctat tactgagcag ctgctgaatg cgcgcgctga tgtgacgctg 1200
ggtggcggag caaaaacctt tgccgaaacc gccactgccg gtgagtggca ggggaaaact 1260
ctgcgcgaac aggcgcaagc ccgcggatat caactggtgt ctgatgcggc gtcgctgaac 1320
tccgtaaccg aagcgaacca gcagaaaccg cttctgggtc tgttcgcaga tggcaatatg 1380
cctgtgcgtt ggctggggcc caaagcaacg tatcacggca acatcgataa gcctgctgta 1440
acgtgtacgc cgaacccgca gcgtaatgat agtgtaccga cactcgcgca gatgaccgat 1500
aaagcaatcg agctgctgtc gaagaacgaa aaaggttttt tcctgcaagt tgagggcgcg 1560
agcattgatc gtcagaacca tgccgctaac ccctgcggcc agatcgggga aacggttgat 1620
ctggatgagg ctgtacagcg tgctctggaa tttgcgaaaa aagagggtaa taccttagtg 1680
attgttaccg cagaccacgc acacgctagc cagatcgttg caccggacac taaggcaccg 1740
ggcctgaccc aggctctgaa caccaaggac ggggcggtta tggttatgtc ctatggtaac 1800
tcggaagagg actcccaaga acataccggt tcgcaattac gcatcgcggc gtatggtccg 1860
catgcagcga acgtagtggg tctgaccgat cagaccgatc tgttctatac aatgaaagcc 1920
gcgttgggac tcaaactgga gggatcccat catcatcacc atcacggtgg cggtggtagc 1980
atgcgccata aaggctcg 1998

<210> SEQ ID NO 7
<211> LENGTH: 736
<212> TYPE: PRT
<213> ORGANISM: Artificial Sequence
<220> FEATURE:
<223> OTHER INFORMATION: Synthesized

<400> SEQUENCE: 7

```
Ala Asp Thr Pro Glu Met Pro Val Leu Glu Asn Arg Ala Ala Gln Gly
1               5                   10                  15

Asp Ile Thr Ala Pro Gly Gly Ala Arg Arg Leu Thr Gly Asp Gln Thr
            20                  25                  30

Ala Ala Leu Arg Asp Ser Leu Ser Asp Lys Pro Ala Lys Asn Ile Ile
        35                  40                  45

Leu Leu Ile Gly Asp Gly Met Gly Asp Ser Glu Ile Thr Ala Ala Arg
    50                  55                  60

Asn Tyr Ala Glu Gly Ala Gly Gly Phe Phe Lys Gly Ile Asp Ala Leu
65                  70                  75                  80

Pro Leu Thr Gly Gln Tyr Thr His Tyr Ala Leu Asn Lys Lys Thr Gly
                85                  90                  95

Lys Pro Asp Tyr Val Thr Asp Ser Ala Ala Ser Ala Thr Ala Trp Ser
            100                 105                 110

Thr Gly Val Lys Thr Tyr Asn Gly Ala Leu Gly Val Asp Ile His Glu
        115                 120                 125

Lys Asp His Pro Thr Ile Leu Glu Met Ala Lys Ala Ala Gly Leu Ala
    130                 135                 140

Thr Gly Asn Val Ser Thr Ala Glu Leu Gln Asp Ala Thr Pro Ala Ala
145                 150                 155                 160

Leu Val Ala His Val Thr Ser Arg Lys Cys Tyr Gly Pro Ser Ala Thr
```

-continued

```
                165                 170                 175

Ser Glu Lys Cys Pro Gly Asn Ala Leu Glu Lys Gly Gly Lys Gly Ser
            180                 185                 190

Ile Thr Glu Gln Leu Leu Asn Ala Arg Ala Asp Val Thr Leu Gly Gly
        195                 200                 205

Gly Ala Lys Thr Phe Ala Glu Thr Ala Thr Ala Gly Glu Trp Gln Gly
    210                 215                 220

Lys Thr Leu Arg Glu Gln Ala Gln Ala Arg Gly Tyr Gln Leu Val Ser
225                 230                 235                 240

Asp Ala Ala Ser Leu Asn Ser Val Thr Glu Ala Asn Gln Gln Lys Pro
                245                 250                 255

Leu Leu Gly Leu Phe Ala Asp Gly Asn Met Pro Val Arg Trp Leu Gly
            260                 265                 270

Pro Lys Ala Thr Tyr His Gly Asn Ile Asp Lys Pro Ala Val Thr Cys
        275                 280                 285

Thr Pro Asn Pro Gln Arg Asn Asp Ser Val Pro Thr Leu Ala Gln Met
    290                 295                 300

Thr Asp Lys Ala Ile Glu Leu Leu Ser Lys Asn Glu Lys Gly Phe Phe
305                 310                 315                 320

Leu Gln Val Glu Gly Ala Ser Ile Asp Arg Gln Asn His Ala Ala Asn
                325                 330                 335

Pro Cys Gly Gln Ile Gly Glu Thr Val Asp Leu Asp Glu Ala Val Gln
            340                 345                 350

Arg Ala Leu Glu Phe Ala Lys Lys Glu Gly Asn Thr Leu Val Ile Val
        355                 360                 365

Thr Ala Asp His Ala His Ala Ser Gln Ile Val Ala Pro Asp Thr Lys
    370                 375                 380

Ala Pro Gly Leu Thr Gln Ala Leu Asn Thr Lys Asp Gly Ala Val Met
385                 390                 395                 400

Val Met Ser Tyr Gly Asn Ser Glu Glu Asp Ser Gln Glu His Thr Gly
                405                 410                 415

Ser Gln Leu Arg Ile Ala Ala Tyr Gly Pro His Ala Ala Asn Val Val
            420                 425                 430

Gly Leu Thr Asp Gln Thr Asp Leu Phe Tyr Thr Met Lys Ala Ala Leu
        435                 440                 445

Gly Leu Lys Leu Glu Gly Gly Gly Gly Ser Asp Val Asp Asn Lys Phe
    450                 455                 460

Asn Lys Glu Gln Gln Asn Ala Phe Trp Glu Ile Leu His Leu Pro Asn
465                 470                 475                 480

Leu Asn Glu Glu Gln Arg Asn Gly Phe Ile Gln Ser Leu Lys Asp Asp
                485                 490                 495

Pro Ser Gln Ser Ala Asn Leu Leu Ala Glu Ala Lys Lys Leu Asn Asp
            500                 505                 510

Ala Gln Ala Pro Lys Gly Gly Gly Gly Ser Thr Tyr Lys Leu Val Ile
        515                 520                 525

Asn Gly Lys Thr Leu Lys Gly Glu Thr Thr Thr Glu Ala Val Asp Ala
    530                 535                 540

Ala Thr Ala Glu Lys Val Phe Lys Gln Tyr Ala Asn Asp Asn Gly Val
545                 550                 555                 560

Asp Gly Glu Trp Thr Tyr Asp Asp Ala Thr Lys Thr Phe Thr Val Thr
                565                 570                 575

Glu Lys Pro Glu Val Ile Asp Ala Ser Glu Leu Thr Pro Ala Val Thr
            580                 585                 590
```

Thr Tyr Lys Leu Val Ile Asn Gly Lys Thr Leu Lys Gly Glu Thr Thr
595 600 605

Thr Glu Ala Val Asp Ala Ala Thr Ala Glu Lys Val Phe Lys Gln Tyr
610 615 620

Ala Asn Asp Asn Gly Val Asp Gly Glu Trp Thr Tyr Asp Asp Ala Thr
625 630 635 640

Lys Thr Phe Thr Val Thr Glu Lys Pro Glu Val Ile Asp Ala Ser Glu
645 650 655

Leu Thr Pro Ala Val Thr Thr Tyr Lys Leu Val Ile Asn Gly Lys Thr
660 665 670

Leu Lys Gly Glu Thr Thr Thr Lys Ala Val Asp Ala Glu Thr Ala Glu
675 680 685

Lys Ala Phe Lys Gln Tyr Ala Asn Asp Asn Gly Val Asp Gly Val Trp
690 695 700

Thr Tyr Asp Asp Ala Thr Lys Thr Phe Thr Val Thr Glu Gly Ser His
705 710 715 720

His His His His His Gly Gly Gly Gly Ser Met Arg His Lys Gly Ser
725 730 735

<210> SEQ ID NO 8
<211> LENGTH: 1998
<212> TYPE: DNA
<213> ORGANISM: Artificial Sequence
<220> FEATURE:
<223> OTHER INFORMATION: Synthesized

<400> SEQUENCE: 8
gcagatacgc ccgaaatgcc cgtgttggag aaccgcgctg cacagggtga tatcacggcc 60
ccaggcggtg cccgtcgcct cacgggagac caaaccgcag ccttgcgtga cagcctttcc 120
gataaacctg caaaaaacat tatcttgctt attggcgacg gtatgggcga ttccgaaatt 180
acggccgcgc gcaattatgc cgaaggcgct ggtggcttct tcaaggggat tgatgcgtta 240
ccactgacag ggcagtacac tcactacgcg ctcaacaaaa aaaccggtaa gccagattac 300
gtaaccgact ctgctgcgag cgccacagcc tggtcaactg gtgtgaaaac ttataacggc 360
gccttaggcg tcgacattca cgaaaaagat cacccgacga ttctggaaat ggcgaaagcg 420
gccggtctgg cgacgggaaa cgtgtctacg gcggaactcc aggacgcgac gcccgccgca 480
ctggtggccc atgtgacctc tcgtaagtgc tacggcccta gtgcgacctc ggagaaatgc 540
ccaggcaatg ctctggaaaa agggggcaag ggttctatta ctgagcagct gctgaatgcg 600
cgcgctgatg tgacgctggg tggcggagca aaaacctttg ccgaaaccgc cactgccggt 660
gagtggcagg ggaaaactct gcgcgaacag gcgcaagccc gcggatatca actggtgtct 720
gatgcggcgt cgctgaactc cgtaaccgaa gcgaaccagc agaaaccgct tctgggtctg 780
ttcgcagatg gcaatatgcc tgtgcgttgg ctggggccca aagcaacgta tcacggcaac 840
atcgataagc ctgctgtaac gtgtacgccg aacccgcagc gtaatgatag tgtaccgaca 900
ctcgcgcaga tgaccgataa agcaatcgag ctgctgtcga agaacgaaaa aggtttttc 960 ctgcaagttg agggcgcgag cattgatcgt cagaaccatg ccgctaaccc ctgcggccag 1020
atcggggaaa cggttgatct ggatgaggct gtacagcgtg ctctggaatt tgcgaaaaaa 1080
gagggtaata ccttagtgat tgttaccgca gaccacgcac acgctagcca gatcgttgca 1140
ccggacacta aggcaccggg cctgacccag gctctgaaca ccaaggacgg ggcggttatg 1200
gttatgtcct atggtaactc ggaagaggac tcccaagaac ataccggttc gcaattacgc 1260
atcgcggcgt atggtccgca tgcagcgaac gtagtgggtc tgaccgatca gaccgatctg 1320
ttctatacaa tgaaagccgc gttgggactc aaactggagg gcggtggggg atccgatgtc 1380
gacaataagt tcaataaaga gcagcagaac gccttctggg agattctcca cctcccgaat 1440
ctgaacgagg agcagcgtaa cggttttatt caatctctga aagacgatcc gtcacagagc 1500
gctaacctgc tggcagaagc aaaaaaatta aatgatgccc aggcgccgaa aggtggcggc 1560
ggttccacgt ataaactcgt catcaacggt aaaacgttaa aaggcgaaac taccactgaa 1620
gctgttgatg ctgctacggc agaaaaagtg ttcaaacagt acgcgaatga caatggcgtg 1680
gatggcgagt ggacttacga tgacgcgact aaaactttca ccgttaccga aaagccggaa 1740
gtaattgacg cttccgaact gaccccggca gtcacgactt acaaattggt cattaacggg 1800
aaaaccctta aaggggaaac caccactaag gcggttgacg cggaaacggc cgagaaagcg 1860
ttcaagcagt atgctaacga caatggtgtt gatggcgtgt ggacctatga tgatgctaca 1920
aaaacattta cggtgaccga aggatcccat catcatcacc atcacggtgg cggtggtagc 1980
atgcgccata aaggctcg 1998

<210> SEQ ID NO 9
<211> LENGTH: 376
<212> TYPE: DNA
<213> ORGANISM: Artificial Sequence
<220> FEATURE:
<223> OTHER INFORMATION: Synthesized

<400> SEQUENCE: 9
gaacaattat cttcaacatg gactaatctt gtccttgaat caagtactgt gatccgccca 60
cgtaccttct cagcttctcc ccaaactgtt agaactcgaa cgtcctatct tcttttgctt 120
ccaccagttg attgccaagt tcctctagtt caaactcatc ccgagttggc cgtttaggta 180
tatttgactt tgccaatgcc gcccctcctt attgaattga gtatcagtct tacaccgata 240
taaaaatcca tgaaaacatt ttacttacaa atagattaag gaaaattttt ctaatataaa 300
tgtttgaaat aatttaccta atttagtata atttgctttg ttgcaaaaat ataccaaaat 360
gagaggagct ttaata 376

<210> SEQ ID NO 10
<211> LENGTH: 44
<212> TYPE: DNA
<213> ORGANISM: Artificial Sequence
<220> FEATURE:
<223> OTHER INFORMATION: Synthesized

<400> SEQUENCE: 10
aaggcgccgc aacttttgat tcgctcaggc gtttaatagg atgt 44

<210> SEQ ID NO 11
<211> LENGTH: 72
<212> TYPE: DNA
<213> ORGANISM: Artificial Sequence
<220> FEATURE:
<223> OTHER INFORMATION: Synthesized

<400> SEQUENCE: 11
atgaaaacaa tacgaacagg catgatgact ttggcggcac tggccgtttt gggaaccaac 60
gtggtagcgg ct 72

<210> SEQ ID NO 12

-continued

```
<211> LENGTH: 69
<212> TYPE: DNA
<213> ORGANISM: Artificial Sequence
<220> FEATURE:
<223> OTHER INFORMATION: Synthesized

<400> SEQUENCE: 12

atgaaaaagg tcgttaacag tgtattggct agtgcactcg cacttactgt tgctcccatg     60

gctttcgct                                                              69


<210> SEQ ID NO 13
<211> LENGTH: 84
<212> TYPE: DNA
<213> ORGANISM: Artificial Sequence
<220> FEATURE:
<223> OTHER INFORMATION: Synthesized

<400> SEQUENCE: 13

atgtcaattt cggtaagatt caagagttta attgctttac ttatgactgt agtattttta     60

ctagtaccaa gttccgcatt cgct                                             84


<210> SEQ ID NO 14
<211> LENGTH: 90
<212> TYPE: DNA
<213> ORGANISM: Artificial Sequence
<220> FEATURE:
<223> OTHER INFORMATION: Synthesized

<400> SEQUENCE: 14

atgaaaaaaa gaagggtcgt taacagtgta ttgcttctgc tactgctagc tagtgcactc     60

gcacttactg ttgctcccat ggctttcgct                                       90
```